(12) United States Patent
Mezler et al.

(10) Patent No.: US 7,906,120 B2
(45) Date of Patent: Mar. 15, 2011

(54) NEUTRALIZING MONOCLONAL ANTIBODIES AGAINST THE NOGO-66 RECEPTOR (NGR)

(75) Inventors: Mario Mezler, Forst (DE); Achim Moeller, Gruenstadt (DE); Reinhold Mueller, Schifferstadt (DE); Bernhard K. Mueller, Neustadt (DE); Tariq Ghayur, Holliston, MA (US); Eve H. Barlow, Wellesley, MA (US); Martin Schmidt, Bensheim (DE); Axel Meyer, Schwetzingen (DE); Nicole E. Teusch, Wuelfrath (DE)

(73) Assignee: Abbott Laboratories, Abbott Park, IL (US)

( * ) Notice: Subject to any disclaimer, the term of this patent is extended or adjusted under 35 U.S.C. 154(b) by 299 days.

(21) Appl. No.: 11/943,770

(22) Filed: Nov. 21, 2007

(65) Prior Publication Data

US 2008/0279859 A1    Nov. 13, 2008

Related U.S. Application Data

(60) Provisional application No. 60/860,256, filed on Nov. 21, 2006.

(51) Int. Cl.
*A61K 39/395* (2006.01)
*C12P 21/08* (2006.01)

(52) U.S. Cl. ............... 424/143.1; 424/172.1; 530/387.9; 530/388.1

(58) Field of Classification Search ........................ None
See application file for complete search history.

(56) References Cited

U.S. PATENT DOCUMENTS

| | | | |
|---|---|---|---|
| 5,585,089 | A | 12/1996 | Queen et al. |
| 5,624,821 | A | 4/1997 | Winter et al. |
| 5,648,260 | A | 7/1997 | Winter et al. |
| 6,210,671 | B1 * | 4/2001 | Co .............................. 424/154.1 |
| 7,612,181 | B2 * | 11/2009 | Wu et al. ...................... 530/387.3 |
| 2002/0012965 | A1 * | 1/2002 | Strittmatter .................. 435/69.1 |

FOREIGN PATENT DOCUMENTS

WO        90/05191    *    5/1990

OTHER PUBLICATIONS

Groves 2000 (Hybridoma 19(3):201-214).*
Babcock, John S. et al., "A novel strategy for generating monoclonal antibodies from single, isolated lymphocytes producing antibodies of defined specificities", PNAS, (Jul. 1996), vol. 93, pp. 7843-7848.
Barton, William A. et al., "Structure and axon outgrowth inhibitor binding of the Nogo-66 receptor and related proteins", The EMBO Journal, (May 2003), vol. 22 No. 13, pp. 3291-3302.
Bird, Robert E. et al., "Single-Chain Antigen-Binding Proteins", Science, (May 1988), vol. 242(4877), pp. 423-426.
Carter, Paul et al., :"Humanization of an anti-p185HER2 antibody for human cancer therapy", PNAS, (May 1992) vol. 89, pp. 4285-4289.
Domeniconi, M. et al., "Myelin-Associated Glycoprotein Interacts with the Nogo66 Receptor to Inhibit Neurite Outgrowth", Neuron, (Jul. 2002), vol. 35, pp. 283-290.
Fontoura, Paulo et al., "Nogo in multiple sclerosis: Growing roles of a growth inhibitor", J. Neurol. Sci, (2006), vol. 245, pp. 201-210.
Fournier Alyson E. et al., "Identification of a receptor mediating Nogo-66 inhibition of axonal regeneration", Letters to Nature, (Jan. 2001), vol. 409, pp. 341-346.
Fournier Alyson E. et al., "Truncated Soluble Nogo Receptor Binds Nogo-66 and Blocks Inhibition of Axon Growth by Myelin", The Journal of Neuroscience, vol. 22(20), pp. 8876-8883, 2002.
Fanger Michael W. et al., "Production and Use of Anti-FcR Bispecific Antibodies", lmmunomethods, (1994), vol. 4, pp. 72-81.
Giege R. et al., "Crystallization of Nucleic Acids and Proteins, a Practical Approach", 2nd. ea., (1999),pp. 20 1-16, Oxford University Press, New York, New York,.
Grandpre Tadzia et al., "Identification of the Nogo inhibitor of axon regeneration as a Reticulon protein", Letters to Nature, (2000), vol. 403, pp. 439-444.
Harlow Ed et al., "Antibodies a Laboratory Manual", (1990), Cold Spring Harbor Press, New York:, Table of Contents Only.
Holliger Philipp et al., "Diabodies": Small bivalent and bispecific antibody fragments, PNAS, (Jul. 1993), vol. 90, pp. 6444-6448.
Hunt David et al., "Nogo Receptor mRNA Expression in Intact and Regenerating CNS Neurons", Molecular and Cellular Neuroscience, (2002), vol. 20, pp. 537-552.
Huston James S. et al., "Protein engineering of antibody binding sites: Recovery of specific activity in an anti-digoxin single-chain Fv analogue produced in *Escherichia coli*", (Aug. 1988), PNAS, vol. 85, pp. 5879-5883.
Johnsson Bo et al., "Immobilization of Proteins to a Carboxymethyldextran-Modified gold Surface for Biospecific Interaction Analysis in Surface Plasmon Resonance Sensors", Analytical Biochemistry, (1991), vol. 198, pp. 268-277.
Johnsson Bo et al., "Comparison of Methods for Immobilization to Carboxymethyl Dextran Sensor Surfaces by Analysis of the Specific Activity of Monoclonal Antibodies", Journal of Molecular Recognition, (1995), vol. 98, pp. 125-131.
Jonsson U. et al., "Real-time Biospecific Interaction Analysis Using Surface Plasmon Resonance and a Sensor Chip Technology", BioTechniques, (1991), vol. 11 No. 5, pp. 620-627.
Jonsson U. et al., "Introducing a biosensor based technology for real-time biospecific interaction analysis", Ann. Biol. Clin., (1993), vol. 51, pp. 19-26.
Kabat Elvin A. et al., "Sequences of Proteins of Immunological Interest" Fifth Edition (1991), U.S. Department of Health and Human Services, Maryland.
Kim Ji-Eun et al., "Nogo-66 Receptor Prevents Raphespinal and Rubrospinal Axon Regeneration and Limits Functional Recovery from Spinal Cord Injury", Neuron, (Oct. 2004), vol. 44, pp. 439-451.

(Continued)

*Primary Examiner* — Daniel E Kolker
(74) *Attorney, Agent, or Firm* — Sreenivasarao Vepachedu

(57) ABSTRACT

The subject invention relates to isolated proteins, particularly monoclonal antibodies, which bind to the Nogo-66 receptor. Specifically, these antibodies have the ability to inhibit the binding of the natural ligand of the Nogo-66 receptor and neutralize the Nogo-66 receptor. These antibodies or portions thereof of the invention are useful for detecting NgR and for inhibiting NgR activity, for example in a human suffering from a disorder in which NgR or Nogo-66 activity is detrimental.

21 Claims, 11 Drawing Sheets
(1 of 11 Drawing Sheet(s) Filed in Color)

OTHER PUBLICATIONS

Kipriyanov, Sergey M. et al., "Single-chain antibody streptavidin fusions: Tetrameric bifunctional scFv-complexes with biotin binding activity and enhanced affinity to antigen", Hum. Antibod. Hybridomas., (1995), vol. 6 (3), pp. 93-101.

Kipriyanov, Sergey M. et al., "Recombinant Single-chain Fv Fragments Carrying C-Terminal Cysteine Residues: Production of Bivalent and Biotinylated Miniantibodies", Molecular Immunology, (1994), vol. 31 No. 14, pp. 1047-1058.

Kohler G. et al., Continuous cultures of fused cells secreting antibody of predefined specificity, Nature, vol. 256, pp. 495-497, 1975.

Lauren Juha et al., "Two novel mammalian Nogo receptor homologs differentially expressed in the central and peripheral nervous systems", Molecular and Cellular Neuroscience, (May 2003), vol. 24, pp. 581-594.

Lee Daniel H. et al., "Targeting the Nogo Receptor to Treat Central Nervous System Injuries", Nature Reviews, (Nov. 2003), vol. 2, pp. 1-7.

Mcgee Aaron W. et al., "The Nogo-66 receptor: focusing myelin inhibition of axon regeneration", Trends in Neurosciences, (Apr. 2003)vol. 26, No. 4, page.

Mi Sha et al., "LINGO-1 is a component of the Nogo-66 receptor/p75 signaling complex", Nature Neuroscience, (Mar. 2004), vol. 7 No. 3, pp. 221-228.

Padlan Eduardo A., "A Possible Procedure for Reducting the Immunogenicity of Antibody Variable Domains While Preserving Their Ligand-Binding Properties", Molecular Immunology, (1991), vol. 28 No. 4/5, pp. 489-498.

Park Jong B. et al, "A TNF Receptor Family Member, TROY, Is a Coreceptor with Nogo Receptor in Mediating the Inhibitory Activity of Myelin Inhibitors", Neuron, (Feb. 3, 2005), vol. 45, pp. 345-351.

Pignot V. et al., "Characterization of two novel proteins, NgRH1 and NgRH2, structurally and biochemically homologous to the Nogo-66 receptor", Journal of Neurochemistry, (2003), vol. 85, pp. 717-728.

Poljak Roberto J, "Production and structure of diabodies", Structure, (Dec. 15, 1994), vol. 2, pp. 1121-1123.

Presta, Leonard G. et al., "Humanization of an Antibody Directed Against IgE", The Journal of Immunology, (Sep. 1, 1993), vol. 151, pp. 2623-2632.

Riechmann Lutz et al., "Reshaping human antibodies for therapy", Nature, (Mar. 1988), vol. 332, pp. 323-327.

Robinson Joseph R., "Sustained and Controlled Release Drug Delivery Systems", (Dec 1978), Marcel Dekker, Inc., New York.

Roguska Michael A. et al., "Humanization of murine monoclonal antibodies through variable domain resurfacing", PNAS, (Feb. 1994), vol. 91, pp. 969-973.

Shao Zhaohui et al., TAJ/TROY, an Orphan TNF Receptor Family Member, Binds Nogo-66 Receptor 1 and Regulates Axonal Regeneration, Neuron, (Feb. 3, 2005), vol. 45, pp. 353-359.

Studnicka Gary M. et al., "Human engineered monoclonal antibodies retain full specific binding activity by preserving non-CDR complementarity-modulating residues", Protein Engineering, (1994), vol. 7 No. 6, pp. 805-814.

Teng Felicia Yu Husan et al., "Why do Nogo/Nogo-66 receptor gene knockouts result in inferior regeneration compared to treatment with neutralizing agents?", Journal of Neurochemistry, (2005), vol. 94, pp. 864-874.

Venkatesh Karthik et al., "The Nogo-66 Receptor Homolog NgR2 Is a Sialic Acid-Dependent Receptor Selective for Myelin-Associated Glycoprotein", The Journal of Neuroscience, (Jan. 26, 2005), vol. 25(4), pp. 808-822.

Wang Xingxing et al., "Localization of Nogo-A and Nogo-66 Receptor Proteins at Sites of Axon-Myelin and Synaptic Contact", The Journal of Neuroscience, (Jul. 1, 2002), vol. 22(13), pp. 5505-5515.

Ward Sally E. et al., "Binding activities of a repertoire of single immunoglobulin variable domains secreted from *Escherichia coli*", Letters to Nature, (Oct. 12, 1989), vol. 341, pp. 544-546.

Woolf Clifford J. et al., "It Takes More Than Two to Nogo", Science (Aug. 16, 2002), vol. 297, pp. 1132-1134.

Wong Scott T. et al., "A p75NTR and Nogo receptor complex mediates repulsive signaling by myelin-associated glycoprotein" Nature Neuroscience, (Dec. 2002), vol. 5 No. 12, pp. 1302-1308.

McCafferty John, et al., "Phage antibodies: filamentous phase displaying antibody variable domains", Letters to Nature, vol. 38, pp. 552-554, (Dec. 1990).

* cited by examiner

Summary Table: Values indicate 50% competition of AP-Nogo66 binding to HEK293f cells expressing recombinant human NgR Deletions are symbolized by a "Δ" symbol.

NEUTRALIZING MONOCLONAL ANTIBODIES AGAINST THE NOGO-66 RECEPTOR (NGR)

This application claims priority to provisional application Ser. No. 60/860,256 filed on Nov. 21, 2006.

TECHNICAL FIELD

The present application describes Nogo-66 receptor binding proteins, particularly monoclonal antibodies, which have the ability to bind to the Nogo-66 receptor and neutralize the function of the Nogo-66 receptor. These antibodies may therefore have utility in the treatment of several states including but not limited to mammalian brain trauma, spinal cord injury, stroke, neurodegenerative diseases, and schizophrenia.

BACKGROUND INFORMATION

Axonal regeneration after injury within the mammalian central nervous system (CNS) is almost always impossible; the outcome depends on the balance between the intrinsic ability of the nerve fibers in the CNS to re-grow, and the inhibitory factors within the CNS, localized in the microenvironment of the lesion site, which actively prevent the re-growth, and thus the regeneration of the injured fiber tracts.

It has been established that CNS myelin, generated by oligodendrocytes, is the most relevant non-permissive factor for axonal growth in the early phase of an injury, by causing growth cone collapse in vitro as well as in vivo, which results in the direct inhibition of axon outgrowth (for review see: Lee et al., 2003). Only recently major inhibitory factors on CNS myelin have been identified: oligodendrocyte myelin glycoprotein (OMgp), Myelin associated glycoprotein (MAG) and Nogo-A (Domeniconi et al., 2002; reviews: Woolf & Bloechinger, 2002; McGee & Strittmatter, 2003; Lee et al., 2003). The latter protein contains a domain Nogo-66; GrandPré et al., 2000), which exerts a main inhibitory function. Interestingly, all three inhibitory proteins show high expression levels in the CNS and interact with the same neuronal glycosylphosphatidylinositol (GPI) moiety-anchored receptor, the Nogo-66 receptor, or NgR (Fournier et al., 2001). The Nogo-66 receptor, NgR, is a 473 amino acid glycosylphosphatidylinositol-linked protein. It consists of an N-terminal signal sequence, followed by 8 leucine-rich repeat domains, a leucine-rich repeat C-terminal domain (together forming the so-called ectodomain) and the GPI-anchoring domain. Through the GPI-anchor, NgR is linked to the external neuronal plasmalemma.

NgR itself belongs to a family of three CNS-enriched GPI-anchored proteins (named NgR, NgR2 and NgR3) with about 40% sequence identity but very similar overall structural organization (Barton et al. 2003; Lauren et al. 2003; Pignot et al. 2003). Although NgR is the only member known to interact with multiple myelin-associated inhibitory molecules, MAG has recently been shown also to interact with NgR2 (Venkatesh et al. 2005). The function of the NgR homologues is currently not known. NgR itself is not expressed during early development in rodents or chick, but shows high expression levels in adult animals; NgR is expressed in most if not all of the CNS regions, including the spinal cord (Hunt et al., 2002a,b). Spinal cord expression has been shown in chick (Fournier et al., 2001), rat (Hunt et al., 2002a) and mouse (Wang et al., 2002b) at both the mRNA and protein level. Within adult CNS tissue, NgR protein is expressed in all mature neurons, including their axonal processes. Ligand binding to NgR initiates an intracellular signaling cascade, which results in axon outgrowth inhibition and growth cone collapse. As NgR does not contain a transmembrane domain, signaling requires a co-receptor, which transduces the NgR/ligand interaction signal into the cell. The initial step in NgR signaling is its interaction with the co-receptors p75 or TROY (Wong et al., 2002; Shao et al., 2005; Park et al., 2005). A second co-receptor has been identified, called Lingo-1. Only a ternary complex between NgR, P75 or TROY and Lingo-1 constitutes the functional signaling complex (Mi et al., 2004; Park et al., 2005). The outcome of this signaling is a rearrangement of the actin cytoskeleton. In the neuron this actin cytoskeletal change causes an inhibition of axon outgrowth and induction of growth cone collapse.

In vitro, dorsal root ganglion cells from NgR (−/−) mice loose Nogo66 binding capacity and are less responsive to the inhibitory effects of Nogo66, Fc-MAG, OMgp or myelin in a growth cone collapse assay (Kim et al., 2004). NgR (−/−) mice demonstrated increased regeneration of brainstem tracts, including rubrospinal and raphespinal tracts, after partial or complete spinal cord injury. Even after a complete experimental transection of the spinal cord, the NgR (−/−) mice showed increased functional recovery in an open field test. Following hemisection and complete transection of the spinal cord, recovery in NgR (−/−) mice was significantly better than in homozygous (+/+) and heterozygous littermates (Kim et al., 2004).

The present application describes the generation of neutralizing monoclonal antibodies against the NgR, which selectively compete for Nogo-66 binding and that are expected to ameliorate disorders in which NgR activity may be detrimental. The neutralizing monoclonal antibodies of the present invention are expected, for example, to promote neuronal regeneration in the injured CNS, specifically after acute spinal cord injury, brain trauma or neurodegenerative diseases such as for example, Huntington's chorea, Parkinson's disease, Alzheimer's disease or multiple sclerosis.

BRIEF DESCRIPTION OF THE FIGURES

The patent or application file contains at least one drawing executed in color. Copies of this patent or patent application publication with color drawing will be provided by the Office upon request and payment of the necessary fee.

LIST OF SEQUENCES

Figure 1A:
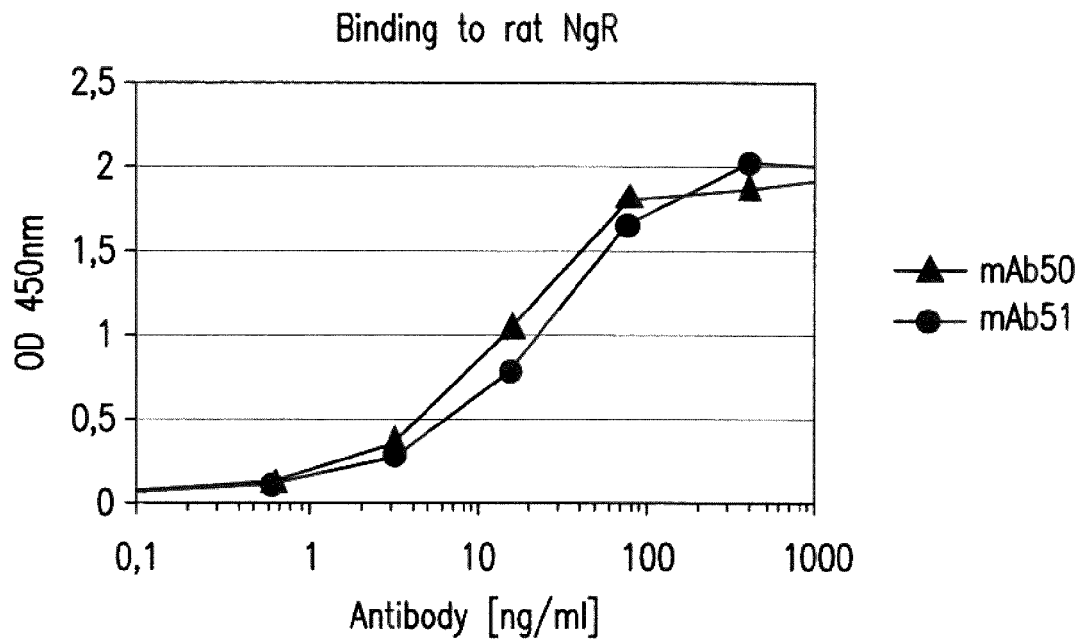
FIGS. 1a and 1b: Antibody mAb50 and mAb51 binding to human and rat NgR.

SEQ ID NO. 1: Human NgR protein
SEQ ID NO. 8: Human NgR nucleotide
SEQ ID NO. 2: Rat NgR protein
SEQ ID NO. 9: rat NgR nucleotide SEQ ID NO. 3: Antibody Clone 50 VH
SEQ ID NO. 4: Antibody Clone 50 VL
SEQ ID NO. 5: Antibody Clone 51 VH
SEQ ID NO. 6: Antibody Clone 51 VL
SEQ ID NO. 7: AP-Nogo-66 protein
SEQ ID NO. 10: AP-Nogo-66 nucleotide

DETAILED DESCRIPTION

The present application relates to isolated binding proteins that interact with the Nogo receptor (NgR), in particular neutralizing monoclonal antibodies that bind to and neutralize human and rat NgR. These antibodies have the capacity to compete with Nogo-66 for binding to NgR. Other aspects of the present application include methods of making, pharmaceutical compositions using the same, and methods of using such binding proteins.

Antibodies

The principal embodiment of the present application comprises isolated proteins or polypeptides that specifically bind to at least one epitope of a Nogo-66 receptor (NgR). The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art. The term "Polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The isolated proteins or polypeptides that specifically bind to at least one epitope of a Nogo-66 receptor (NgR) are capable of inhibiting binding of a ligand to said NgR. The Nogo-66 receptor, NgR, is a 473 amino acid glycosylphosphatidylinositol-linked protein. It consists of an N-terminal signal sequence, followed by 8 leucine-rich repeat domains, a leucine-rich repeat C-terminal domain (together forming the so-called ectodomain) and the GPI-anchoring domain. Through the GPI-anchor, NgR is linked to the external neuronal plasmalemma. Preferred proteins of the present invention are monoclonal neutralizing antibody or antigen-binding fragment thereof that bind to at least one epitope of the human NgR. Nogo 66 is one of the several major inhibitory factors on CNS myelin that induces inhibition of axon outgrowth and promotes collapse of cone growth.

The term "antibody", as used herein, is intended to refer to immunoglobulin molecules comprised of four polypeptide chains, two heavy (H) chains and two light (L) chains interconnected by disulfide bonds. An antibody is said to be "capable of binding" a molecule if it is capable of specifically reacting with the molecule to thereby bind the molecule to the antibody. The term "epitope" is meant to refer to that portion of any molecule capable of being bound by an antibody, which can also be recognized by that antibody. Epitopes or "antigenic determinants" usually consist of chemically active surface groupings of molecules such as amino acids or sugar side chains and have specific three-dimensional structural characteristics as well as specific charge characteristics.

The term "antigen-binding fragment" of an antibody (or simply "antigen fragment"), as used herein, refers to one or more portions of an antibody that retain(s) the ability to specifically bind the receptor and activate or modulate it, respectively. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al. (1989) Nature 341:544-546), which consists of a VH domain; and (vi) an isolated CDR. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv) antibodies. (See, e.g., Bird et al. (1988) Science 242:423-426; Huston et al. (1988) Proceedings of the National Academy of Science USA 85:5879-5883.) Such scFv antibodies are also intended to be encompassed within the term antigen-binding portion of an antibody. Other forms of single chain antibodies, such as diabodies are also encompassed within the term. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites on the same receptor or across two receptor molecules. (See, e.g., Holliger et al. (1993) Proceedings of the National Academy of Science USA 90:6444-6448; Poljak et al. (1994) Structure 2:1121-1123.)

A "monoclonal antibody" as used herein is intended to refer to a preparation of antibody molecules, which share a common heavy chain and common light chain amino acid sequence, in contrast with "polyclonal" antibody preparations that contain a mixture of different antibodies. Monoclonal antibodies can be generated by several novel technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) Nature 256:495-497). The antibodies of the present invention were generated by standard immunization/hybridoma technique in mice using NgR protein generated in a mammalian cell line.

A "neutralizing monoclonal antibody" as used herein is intended to refer to a preparation of antibody molecules, which upon binding to the specific antigen are able to compete and inhibit the binding of the natural ligand for said antigen. In the specific case of the present application, the neutralizing antibodies of the present invention are capable to compete with Nogo66 for binding to the NgR, and to prevent Nogo66 biological activity or function that would result from binding of Nogo66 to NgR.

Preferably, the monoclonal neutralizing antibody of the present application is a human antibody. The term "human antibody" refers to antibodies having variable and constant regions corresponding to, or derived from, human germline immunoglobulin sequences (e.g., see Kabat et al. *Sequences* of Proteins of Immunological Interest, Fifth Edition, U.S. Department of Health and Human Services, NIH Publication No. 91-3242, 1991). The human antibodies of the present application, however, may include amino acid residues not encoded by human germline immunoglobulin sequences (e.g., mutations introduced by random or site-specific mutagenesis in vitro or by somatic mutation in vivo), for example, in the CDRs and, in particular, CDR3. As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. In various embodiments, the antibody is a recombinant antibody or a monoclonal antibody. The most preferred neutralizing antibodies of the present application are referred to herein as mAb50 and mAb51 (ATCC No. PTA-8383 and PTA-8384, respectively). mAb50 and mAb51 antibodies and functional antibody fragments, mAb50- and mAb51-related antibodies and functional antibody fragments, and other antibodies and functional antibody fragments with equivalent properties to mAb50 and mAb51, such as high affinity binding to NgR with low dissociation kinetics and high neutralizing capacity, are intended as part of the present invention.

The binding affinity and dissociation rate of an anti-NgR antibody of the present application to an immunogenic NgR polypeptide or fragment thereof, may be determined by any method known in the art. For example, the binding affinity can be measured by competitive ELISAs, c RIAs, BIAcore or KinExA technology. The dissociation rate also can be measured by BIAcore or KinExA technology. The binding affinity and dissociation rate are measured by surface plasmon resonance using, e.g., a BIAcore.

One of the preferred antibodies of the present application has at least 90% amino acid sequence identity with a sequence comprising a heavy chain variable region (VH region) comprising the sequence of SEQ ID NO: 3 and a light chain variable region (VL region) comprising the sequence of SEQ ID NO: 4, the mAB50 antibody. Another preferred embodiment has at least 90% amino acid sequence identity with a sequence comprising a heavy chain variable region (VH region) comprising the sequence of SEQ ID NO: 5 and a light chain variable region (VL region) comprising the sequence of SEQ ID NO: 6, the mAB51 antibody.

Preferably, the mAb50 and mAb51 antibodies bind human NgR with a $EC_{50}$ of less than $1\times10^{-9}$ M, more preferably the antibodies bind to NgR with a $EC_{50}$ below $1\times10^{-10}$, and most preferably the antibodies bind to NgR with an $EC_{50}$ below $4\times10^{-11}$ M.

It is intended that the anti-NgR antibodies mAb50 and mAb51 bind to human NgR in various forms, including pro-NgR, mature NgR and truncated NgR. The antibodies mAb50 and mAb51 do not specifically bind to other NgR homologues, like NgR2 or NgR3, or other LRR-containing proteins. However, the antibodies mAb50 and mAb51 do exhibit cross reactivity to NgR from other species, in particular rodents and more specifically rat NgR5. MAb52 through 62 additionally are cross-reactive to mouse NgR. For example, the antibodies bind to NgR from rat ($IC_{50}$ of both antibodies for rat NgR is about $3\times10^{-11}$ M).

It is also intended that the isolated binding proteins that interact with (NgR) of the present application may be a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Protein glycosylation depends on the amino acid sequence of the protein of interest, as well as the host cell in which the protein is expressed. Different organisms may produce different glycosylation enzymes (eg., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

The antibodies of the present application comprise a heavy chain constant region, such as an IgG1, IgG2, IgG3, IgG4, IgA, IgE, IgM or IgD constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment. Replacements of amino acid residues in the Fc portion to alter antibody effector's function are known in the art (Winter, et al. U.S. Pat. Nos. 5,648,260; 5,624,821). The Fc portion of an antibody mediates several important effector's functions e.g. cytokine induction, ADCC, phagocytosis, complement dependent cytotoxicity (CDC) and half-life/clearance rate of antibody and antigen-antibody complexes. In some cases these effector's functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fcγ Rs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector's functions of the antibody are altered.

Generation of Recombinant Proteins

For immunization and for the ELISA assays, as well as for the neurite outgrowth assays (described in the "Examples" section), soluble recombinant human and rat NgR's were produced. Also, the ligand Nogo66, fused to a alkaline phosphatase tag (AP-Nogo66) was generated and served as inhibitory factor for neurite outgrowth assays as well as a ligand in the ELISA and FACS studies (also described in the "Examples" section).

Human and Rat NgR

The human NgR protein was based on accession number AAG53612. The protein DNA (for amino acids 27 to 450) was cloned into a pSec vector (Ambion), and the protein was generated by stable expression in CHO-K1 cells. The expressed receptor consisted of 424 amino acids of the complete protein (the amino acids 27 to 450), coupled to a Myc and 6× His tag (SEQ ID NO: 12) at the C-terminus according to SEQ ID No. 1: Human NgR protein and SEQ ID NO. 8: Human NgR nucleotide. Human secNgR 27-450 aa_D6_CHO-K1 cells were cultivated in eight 40-chamber cell factories with 5000 ml UltraCHO serum-free medium (Cambrex Bio Science) per cell factory until confluence (ca. 5 days). Then the 401 supernatant was centrifuged and concentrated up to 500 ml with Hemoflow F columns (Fresenius Medical Care). The concentrate was frozen at −80° C. For the protein purification the concentrated protein supernatant was filled to 1000 ml with 500 ml 20 mM $NaH_2PO_4$; 140 mM NaCl; pH 7.4 and concentrated again to 300 ml. The concentration process was repeated once again and finally 300 ml 20 mM $NaH_2PO_4$; 140 mM NaCl; pH 7.4 was added to the concentrate. 50 ml Ni-NTA-Superflow Fa. (Qiagen catalog #30430), equilibrated with 20 mM $NaH_2PO_4$; 300 mM NaCl; pH 8.0 was added to the 600 ml concentrate, stirred for 1 h at 6° C., let settle down at 6° C., supernatant discarded and Ni-NTA beads filled in a column. Column was washed at room temperature with 10 CV 20 mM $NaH_2PO_4$; 300 mM NaCl; pH 8.0 followed by a 5-10 CV 20 mM $NaH_2PO_4$; 300 mM NaCl; 10 mM Imidazole; pH 8.0. The column was eluted with 20 mM $NaH_2PO_4$; 300 mM NaCl; 100 mM Imidazole; pH 8.0 and collect the UV-280 nm active peak. The eluate was subsequently dialyzed over night at 6° C. against 5 L 25 mM Tris/HCl; pH 7.0 and the dialysate loaded at room temperature on a Q-Sepharose column (column size 1.6 cm×3 cm; volume 6 ml; Amersham Biosciences catalog #17-0510-01). Buffer A was 50 mM Tris/HCl; pH 7.0. Buffer B was 50 mM Tris/HCl; 1M NaCl; pH 7.0, at a flow rate of 2 ml/min. Gradient was 0% B hold 5 CV; 0-50% B in 12 CV; 50-100% B in 2 CV; hold 100% B 5 CV. The fraction size was 2.5 ml. Subsequently, the fractions were analyzed on SDS-PAGE, the fractions pooled due to their size on SDS-page and purity (the highest NgR-His purity for the high glycosylated NgR-His; with the highest NgR-His purity for the low glycosylated NgR-His). The pooled fractions were dialyzed once more against 20 mM $NaH_2PO_4$; 140 mM NaCl; pH 7.4 in a 12-14 kDa dialysing tube at 6° C., the fraction filtered through a 0.2 μm sterile filter and stored at 6° C. for further use. For long time storage the receptor fractions were aliquoted and stored at −80° C.

The rat NgR DNA (accession number AAM46772) was cloned into pcDNA3.1 (Invitrogen), and expressed and produced in a transient expression system in HEK293F cells. The protein contained amino acids 27 through 450 coupled to a 6×His tag (SEQ ID NO: 12) according to SEQ ID NO. 2: Rat NgR protein and SEQ ID NO. 9: rat NgR nucleotide. The production of the rat protein was through standard transient expression for 48-72 hours in HEK293F cells. Cellular supernatant was harvested and the purification of the protein followed similar steps as described above for the human protein. In some experiments proteins from R&D Systems were used. These included human recombinant NgR/Fc chimera, Cat. Number 1208-NG and Recombinant Mouse Nogo Receptor/Fc Chimera, Cat. Number 1440-NG.

Cell Surface Expression of NgR

For NgR expressed on cell surface, the full-length receptor sequence (rat AAM46772 and human AAG53612, respectively) comprising the complete open reading frame from amino acids 1 through 473 was cloned into pcDNA4. The plasmids were transfected into CHO-K1 or HEK293 cells under standard procedures. Briefly, cells were seeded in Petri dishes in MEM medium, transfected with Fugene 6 (Roche) according to the manufacturer. Selection was carried out with 150 μg/ml Zeozin for 2-3 weeks and protein expression verified by FACS (see example 4 below).

For transient expression in HEK293F cells, cells were transfected in suspension according to the manufacturer (Invitrogen; Free Style System), harvested after 48 to 72 hours and used for FACS studies (see Examples section).

Production of AP-Nogo66

AP-Nogo66 (SEQ ID NO. 7 and SEQ ID NO. 10) was produced under standard conditions. Briefly, Nogo66 was cloned into the pAPTag5 vector, HEK293 cells were transfected with the construct and selected with RPMI Glutamax+ 10% FCS, 150 μg/ml Zeocin. For protein production HEK293 cells were cultivated in six 10 chamber cell factories with 1200 ml RPMI (Invitrogen) plus 10% FCS per cell factory until confluence (ca. 3 days). Then the supernatant was discarded and 1200 ml Pro293a-CDM (Cambrex Bio Science) were filled in each cell factory. The cells were cultivated for further 3 days. Afterwards the 7200 ml supernatant was centrifuged and concentrated up to 350 ml with Hemoflow F columns (Fresenius Medical Care). After addition of 1 mM PefablocSC (ROCHE) the concentrate was aliquoted and frozen at −80° C.

Production of Antibodies and Antibody Generating Cell Lines

Antibodies of the application can be generated by immunization of a suitable host (e.g., vertebrates, including humans, mice, rats, sheep, goats, pigs, cattle, horses, reptiles, fishes, amphibians, and in eggs of birds, reptiles and fish). Such antibodies may be polyclonal or monoclonal. To generate the antibodies of the present application, the host is immunized with an immunogenic NgR polypeptide or fragment thereof of the invention. The term "immunization" refers herein to the process of presenting an antigen to an immune repertoire whether that repertoire exists in a natural genetically unaltered organism, or a transgenic organism, including those modified to display an artificial human immune repertoire. Similarly, an "immunogenic preparation" is a formulation of antigen that contains adjuvants or other additives that would enhance the immunogenicity of the antigen.

Immunization of animals may be done by any method known in the art. See, e.g., Harlow and Lane, Antibodies: A Laboratory Manual, New York: Cold Spring Harbor Press, 1990. Methods for immunizing non-human animals such as mice, rats, sheep, goats, pigs, cattle and horses are well known in the art. See, e.g., Harlow and Lane and U.S. Pat. No. 5,994,619. In a preferred embodiment, the NgR antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

It is contemplated that the animal host is immunized with NgR associated with the cell membrane of an intact or disrupted cell and antibodies of the present application are identified by binding to an immunogenic NgR polypeptide of the invention.

After immunization of the animal host with an NgR antigen, antibodies and/or antibody-producing cells may be obtained from the animal. An anti-NgR antibody-containing serum is obtained from the animal by bleeding or sacrificing the animal. The serum may be used as it is obtained from the animal, an immunoglobulin fraction may be obtained from the serum, or the anti-NgR antibodies may be purified from the serum. Serum or immunoglobulins obtained in this manner are polyclonal, thus having a heterogeneous array of properties.

Antibody Producing Cell Lines

The present application also describes antibody-producing immortalized hybridomas that may be prepared from the immunized animal. Preferably, the immunized animal is a non-human animal that expresses human immunoglobulin genes and the splenic B cells are fused to a myeloma derived from the same species as the non-human animal.

After immunization, the animal is sacrificed and the splenic B cells are fused to immortalized myeloma cells as is well known in the art. See, e.g., Harlow and Lane, supra. Preferably, the myeloma cells do not secrete immunoglobulin polypeptides (a non-secretory cell line). After fusion and antibiotic selection, the hybridomas are screened using NgR, or a portion thereof, or a cell expressing NgR. Preferably, the initial screening is performed using an enzyme-linked immunoassay (ELISA) or a radioimmunoassay (RIA), preferably an ELISA (an example of ELISA screening is provided in the Examples section).

Anti-NgR antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art. In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-NgR antibody.

The present application also describes recombinant antibodies that are generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) Proc. Natl. Acad. Sci. USA 93:7843-7848. In this method, single cells secreting antibodies of interest, e.g., lymphocytes derived from any immunized animals, are screened using an antigen-specific hemolytic plaque assay, wherein the antigen NgR, or a fragment thereof, is coupled to sheep red blood cells using a linker, such as biotin, and used to identify single cells that secrete antibodies with specificity for NgR. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to NgR.

Antibodies Generated In Vitro

In vitro methods also can be used to make the antibodies described in the present application, wherein an antibody library is screened to identify an antibody having the desired binding specificity. Methods for such screening of recombinant antibody libraries are well known in the art.

The recombinant antibody library may be from a subject immunized with NgR, or a portion of NgR. Alternatively, the recombinant antibody library may be from a naïve subject, i.e., one who has not been immunized with NgR, such as a human antibody library from a human subject who has not been immunized with human NgR. Antibodies of the present application are selected by screening the recombinant antibody library with the peptide comprising human NgR (e.g., a peptide corresponding to a portion of hNgR) to thereby select those antibodies that recognize NgR. Methods for conducting such screening and selection are well known in the art, such as described in the references in the preceding paragraph. To select antibodies of the present application having particular binding affinities for hNgR, such as those that dissociate from human NgR with a particular $k_{off}$ rate constant, the art-known method of surface plasmon resonance can be used to select antibodies having the desired $k_{off}$ rate constant. To select antibodies of the present application having a particular neutralizing activity for hNgR, such as those with a particular $IC_{50}$, standard methods known in the art for assessing the inhibition of hNgR activity may be used.

Characteristics of the Antibodies

The mAB50 and mAB51 of the present application, or antigen-binding portion thereof, bind human NgR, and dissociates from human NgR with a $k_{off}$ rate constant of about 0.1 $s^{-1}$ or less, preferably $1 \times 10^{-2}$ $s^{-1}$ or less, more preferably $1 \times 10^{-3}$ $s^{-1}$ or less, even more preferably $1 \times 10^{-4}$ $s^{-1}$ or less, most preferably $1 \times 10^{-5}$ $s^{-1}$ or less as determined by surface plasmon resonance. The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

TABLE 1

Individual Biacore Kinetic Rate Parameters
(Antigen: hNgR-Fc chimera)

| Captured antibody | Isotype | On-rate (M−1s−1) | Off-rate (s−1) | Kd (M) |
|---|---|---|---|---|
| mAb50 | IgG2a, k | $3.51 \times 10^5$ | $4.97 \times 10^{-5}$ | $1.41 \times 10^{-10}$ |
| mAb51 | IgG2a, k | $5.44 \times 10^5$ | $5.88 \times 10^{-5}$ | $1.08 \times 10^{-10}$ |

The term "$K_{on}$", as used herein, is intended to refer to the on rate constant for association of an antibody to the antigen to form the antibody/antigen complex as is known in the art.

The term "$K_{off}$", as used herein, is intended to refer to the off rate constant for dissociation of an antibody from the antibody/antigen complex as is known in the art. The term "$K_d$", as used herein, is intended to refer to the dissociation constant of a particular antibody-antigen interaction as is known in the art.

Alternatively, the antibody mAb50 and mAb51 of the present application, or an antigen-binding portion thereof, may inhibit human NgR activity with an $IC_{50}$ of about $1 \times 10^{-6}$ M or less, preferably $1 \times 10^{-7}$ M or less, preferably $1 \times 10^{-8}$ M or less, more preferably $1 \times 10^{-9}$ M or less, more preferably $1 \times 10^{-10}$ M or less, and most preferably $1 \times 10^{-11}$ M or less. The term $IC_{50}$, as used herein, is intended to refer to the concentration of an antibody that competes for binding of the ligand Nogo66 to NgR.

Fusion Antibodies and Immunoadhesins

The present application also describes a fusion antibody or immunoadhesin that may be made which comprises all or a portion of an anti-Nogo receptor-1 antibody of the present application linked to another polypeptide. In some embodiments, only the variable region of the anti-Nogo receptor-1 antibody is linked to the polypeptide. In other embodiments, the VH domain of an anti-Nogo receptor-1 antibody of this application is linked to a first polypeptide, while the VL domain of the antibody is linked to a second polypeptide that associates with the first polypeptide in a manner that permits the VH and VL domains to interact with one another to form an antibody binding site. In other embodiments, the VH domain is separated from the VL domain by a linker that permits the VH and VL domains to interact with one another (see below under Single Chain Antibodies). The VH-linker-VL antibody is then linked to a polypeptide of interest. The fusion antibody is useful to directing a polypeptide to a cell or tissue that expresses a Nogo receptor-1 ligand. The polypeptide of interest may be a therapeutic agent, such as a toxin, or may be a diagnostic agent, such as an enzyme; that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

One embodiment provides a labeled binding protein wherein an antibody or antibody portion of the present application is derivatized or linked to another functional molecule (e.g., another peptide or protein). For example, a labeled binding protein of the present application can be derived by functionally linking an antibody or antibody portion of the present application (by chemical coupling, genetic fusion, noncovalent association or otherwise) to one or more other molecular entities, such as a nucleic acid, another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

Useful detectable agents with which an antibody or antibody portion of the present application may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a nucleic acid, biotin, and detected through indirect measurement of avidin or streptavidin binding.

Another embodiment of the present application provides a crystallized binding protein. The term "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999).

Preferably the present application describes crystals of whole anti-NgR antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art.

Single Chain Antibodies

The present application includes a single chain antibody (scFv) that binds an immunogenic NgR of the invention. To produce the scFv, VH- and V-encoding DNA is operatively linked to DNA encoding a flexible linker, e.g., encoding the amino acid sequence (G1Y4-Ser) (SEQ ID NO: 11), such that the VH and VL sequences can be expressed as a contiguous single-chain protein, with the VL and VH regions joined by the flexible linker (see e.g., Bird et al. (1988) Science 242: 423-42 6; Huston et al. (1988) Proc. Natl. Acad. Sci. USA 85: 5879-5883; McCafferty et al., 30 Nature (1990) 34 8: 552-554). The single chain antibody may be monovalent, if only a single VH and VL are used, bivalent, if two VH and VL are used, or polyvalent, if more than two VH and VL are used.

Chimeric Antibodies

The present application further includes a bispecific antibody or antigen-binding fragment thereof in which one specificity is for an immunogenic Nogo receptor-1 polypeptide of the present application. For example, a chimeric antibody can be generated that specifically binds to an immunogenic NgR polypeptide of the invention through one binding domain and to a second molecule through a second binding domain. The term "chimeric antibody" refers to antibodies which comprise heavy and light chain variable region sequences from one species and constant region sequences from another species, such as antibodies having murine heavy and light chain variable regions linked to human constant regions. The chimeric antibody can be produced through recombinant molecular biological techniques, or may be physically conjugated together. In addition, a single chain antibody containing more than one VH and VL may be generated that binds specifically to an immunogenic polypeptide of the invention and to another molecule that is associated with attenuating myelin mediated growth cone collapse and inhibition of neurite outgrowth and sprouting. Such bispecific antibodies can be generated using techniques that are well known for example, Fanger et al. Immunol Methods 4: 72-81 (1994) and Wright and Harris, 20 (supra). In some embodiments, the chimeric antibodies are prepared using one or more of the variable regions from an antibody of the invention. In another embodiment, the chimeric antibody is prepared using one or more CDR regions from said antibody. The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. One type of humanized antibody is a CDR-grafted antibody in which human CDR sequences are introduced into nonhuman VH and VL sequences to replace the corresponding nonhuman CDR sequences.

Humanized Antibodies

Humanized antibodies are antibody molecules from non-human species that binds the desired antigen having one or more complementarity determining regions (CDRs) from the non-human species and framework regions from a human immunoglobulin molecule. Known human Ig sequences are known in the art. Such imported sequences can be used to reduce immunogenicity or reduce, enhance or modify binding, affinity, on-rate, off-rate, avidity, specificity, half-life, or any other suitable characteristic, as known in the art. Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994).

Derivatized and Labeled Antibodies

An antibody or an antigen-binding fragment of the present application can be derivatized or linked to another molecule (e.g., another peptide or protein). In general, the antibody or antigen-binding fragment is derivatized such that binding to an immunogenic polypeptide of the invention is not affected adversely by the derivatization or labeling. For example, an antibody or antibody portion of the present application can be functionally linked (by chemical coupling, genetic fusion, noncovalent association or otherwise) to one or more other molecular entities, such as another antibody (e.g., a bispecific antibody or a diabody), a detection reagent, a cytotoxic agent, a pharmaceutical agent, and/or a protein or peptide that can mediate association of the antibody or antigen-binding fragment with another molecule (such as a streptavidin core region or a polyhistidine tag). Still further, an antibody or antigen-binding portion thereof may be part of a larger immunoadhesion molecule, formed by covalent or non-covalent association of the antibody or antibody portion with one or more other or different proteins or peptides. Examples of such immunoadhesion molecules include use of the streptavidin core region to make a tetrameric scFv molecule (Kipriyanov et al. (1995) Human Antibodies and Hybridomas 6:93-101) and use of a cysteine residue, a marker peptide and a C-terminal polyhistidine tag to make bivalent and biotinylated scFv molecules (Kipriyanov et al. (1994) Molecular Immunology 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

A derivatized antibody may be produced by crosslinking two or more antibodies (of the same type or of different types, e.g., to create bispecific antibodies). Suitable crosslinkers include those that are heterobifunctional, having two distinctly reactive groups separated by an appropriate spacer (e.g. m-maleimidobenzoyl-N-hydroxysuccinimide ester) or homobifunctional (e.g., disuccinimidyl suberate). Such linkers are available from Pierce Chemical Company, Rockford, Ill.

A derivatized antibody may also be a labeled antibody. For instance, detection agents with which an antibody or antibody portion of the invention may be derivatized are fluorescent compounds, including fluorescein, fluorescein isothiocyanate, rhodamine, 5-dimethylamine-1-naphthalenesulfonyl chloride, phycoerythrin, lanthanide phosphors and the like. An antibody also may be labeled with enzymes that are useful for detection, such as horseradish peroxidase, galactosidase, luciferase, alkaline phosphatase, glucoseoxidase and the like. In embodiments that are labeled with a detectable enzyme, the antibody is detected by adding additional reagents that the enzyme uses to produce a detectable reaction product. For example, horseradish peroxidase with hydrogen peroxide and diaminobenzidine. An antibody also may be labeled with biotin, and detected through indirect measurement of avidin or streptavidin binding. An antibody may also be labeled with a predetermined polypeptide epitope recognized by a secondary reporter (e.g., leucine zipper pair sequences, binding sites for secondary antibodies, metal binding domains, epitope: tags). An anti-Nogo receptor-1 antibody or an antigen fragment thereof also may be labeled with a radio-labeled amino acid. The radiolabel may be used for both diagnostic and therapeutic purposes. The radio-labeled anti-Nogo receptor-1 antibody may be used diagnostically, for example, for determining Nogo receptor-1 levels in a subject. Further, the radio-labeled anti-Nogo receptor-1 antibody may be used therapeutically for treating spinal cord injury.

Examples of labels for polypeptides include, but are not limited to, the following radioisotopes or radionucleotides $^{15}N$, $^{35}S$, $^{90}Y$, $^{99}Tc$, $^{111}In$, $^{125}I$, $^{131}I$, $^{177}Lu$, $^{166}Ho$, $^{153}S$. An anti-Nogo receptor-1 antibody or an antigen fragment thereof may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding. Also, a label for polypeptides can include a nucleic acid, for example DNA for detection by PCR, or enhancing gene expression, or siRNA to suppress gene expression in NgR-bearing cells or tissues.

The class and subclass of anti-Nogo receptor-1 antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various classes and subclasses of immunoglobulins, and determining the class and subclass of the antibodies.

Inhibition of NgR Activity by Anti-NgR Antibodies

The anti-Nogo receptor-1 antibodies of the present application, or an antigen-binding fragment thereof, inhibit the binding of a ligand to NgR. The $IC_{50}$ of such inhibition can be measured by any method known in the art, e.g., by ELISA, RIA, or functional antagonism. The $IC_{50}$ may vary between 0.01 and 100 nM. Preferably, the $IC_{50}$ is between 1 and 10 nM. More preferably, the $IC_{50}$ of anti-Nogo receptor-1 antibodies of the present invention, or an antigen-binding fragment thereof, is between 0.1 nM and 1 nM. Most preferably, the $IC_{50}$ is below 0.1 nM.

Dual Variable Domain Antibodies

Dual variable domain (DVD) binding proteins as used herein, are binding proteins that comprise two or more antigen binding sites and are tetravalent or multivalent binding proteins. The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Such DVDs may be monospecific, i.e capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. patent application Ser. No. 11/507, 050 and incorporated herein by reference. It is intended that the present invention comprises a DVD binding protein comprising binding proteins capable of binding NgR. Preferably the DVD binding protein is capable of binding NgR and a second target. The second target is selected from the group consisting of repulsive guidance molecule (RGM), Nogo-A, MAG, OMgp, CSPG. Among CSPG one may choose from aggrecan, brevican, versican, neurocan, phosphacan or Te38. Therefore, these examples comprise myelin-derived inhibitors, as well as known neuronal co-receptors of NgR.

Dual-Specific Antibodies

The present application also describes "dual-specific antibody" technology. Dual-specific antibodies may serve as agonists, antagonists, or both in different combinations. The term "agonist", as used herein, refers to a modulator that, when contacted with a molecule of interest, causes an increase in the magnitude of a certain activity or function of the molecule compared to the magnitude of the activity or function observed in the absence of the agonist. The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological activity of Nogo-66. Antagonists and inhibitors of Nogo-66 may include, but are not limited to any molecules, preferably monoclonal antibodies that interact with the Nogo-66 receptor (NgR).

It should be noted that the interaction with NgR may result in binding and neutralization of the receptor or other ligands/cell membrane components, and may be useful for additive or synergistic functioning against multiple diseases.

The present application also describes NgR antibodies combined with NgR co-receptors, like NgR and p75, NgR and TROY, NgR and LINGO-1. It also comprises antibodies cross-reacting between NgR and its ligand and NgR and myelin-derived inhibitory factors. These may comprise antibodies cross-reacting between NgR and repulsive guidance molecule (RGM), NGR and Nogo-A, NGR and MAG, NgR and OMpg, NgR and CSPG. Among CSPG one may choose from aggrecan, brevican, versican, neurocan, phosphacan or Te38. Therefore, these examples comprise myelin-derived inhibitors, as well as known neuronal co-receptors of NgR.

The present application also describes dual specific antibodies between NgR and growth factor receptors including, but not limited to, nerve growth factor (NGF), brain-derived neurotropic factor (BDNF), epidermal growth factor (EGF), granulocyte-colony stimulating factor (G-CSF), granulocyte-macrophage colony stimulating factor (GM-CSF), neurotrophins, platelet-derived growth factor (PDGF), erythropoietin (EPO), thrombopoietin (TPO), myostatin (GDF-8), Growth Differentiation factor-9 (GDF9) basic fibroblast growth factor (bFGF or FGF2), glial-derived neurotrophic factor (GDNF), ciliary neurotrophic factor (CNTF).

Uses of the Antibodies

Given their ability to bind to human NgR, the neutralizing antibodies of the present application, or portions thereof, can be used to detect human NgR (e.g., in a biological sample, such as serum or plasma), using a conventional immunoassay, such as an enzyme linked immunosorbent assays (ELISA), a radioimmunoassay (RIA) or tissue immunohistochemistry. The present application provides a method for detecting human NgR in a biological sample comprising contacting a biological sample with an antibody, or antibody portion, of the invention and detecting either the antibody (or antibody portion) bound to human NgR or unbound antibody (or antibody portion), to thereby detect human NgR in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include 3H, 14C, $^{35}$S, $^{90}$Y, $^{99}$Tc, $^{111}$In, $^{125}$I, $^{131}$I, $^{177}$Lu, $^{166}$Ho, $^{153}$Sm.

The antibodies and antibody portions of the present application preferably are capable of neutralizing human NgR activity both in vitro and in vivo. Accordingly, such antibodies and antibody portions of the invention can be used to inhibit Nogo-66 binding to NgR or the resulting activity. In another embodiment, the present application provides a method for reducing Nogo-66 activity or NgR activity in a subject, advantageously from a subject suffering from a disease or disorder in which NgR resulting activity is detrimental. The present application provides methods for reducing NgR activity in a subject suffering from such a disease or disorder, which method comprises administering to the subject an antibody or antibody portion of the present application such that NgR activity in the subject is reduced. Preferably, the NgR is human and the subject is a human subject. Alternatively, the subject can be a mammal expressing an NgR to which an antibody of the invention is capable of binding. Still further the subject can be a mammal into which NgR has been introduced. An antibody of the present application can be administered to a human subject for therapeutic purposes. Moreover, an antibody of the present application can be administered to a non-human mammal expressing an NgR with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which NgR activity is detrimental" is intended to include diseases and other disorders in which the presence of NgR or the resulting activity in a subject suffering from the disorder has been shown to be or is suspected of being either responsible for the pathophysiology of the disorder or a factor that contributes to a worsening of the disorder. Accordingly, a disorder in which NgR activity is detrimental is a disorder in which reduction of NgR activity is expected to alleviate the symptoms and/or progression of the disorder. Non-limiting examples of disorders that can be treated with the antibodies of the invention include those disorders discussed in the section below pertaining to pharmaceutical compositions of the antibodies of the invention.

It is recognized that NgR plays an important role in the pathology associated with a variety of diseases involving neurological diseases associated with neurodegeneration or inhibition of neuroregenerative processes, resulting in paralysis. This includes Amytropic Lateral Sclerosis, Brachial Plexus Injury, Brain Injury, including traumatic brain injury, Cerebral Palsy, Friedrich's Ataxia, Guillain-Barré Syndrome, Leukodystrophies, Multiple Sclerosis, Post Polio, Spina Bifida, Spinal Cord Injury, Spinal Muscle Atrophy, Spinal Tumors, Stroke, Transverse Myelitis. Furthermore it is recognized that NgR plays a role in dementia, senile dementia, mild cognitive impairment, Alzheimer-related dementia, Huntington's chorea, tardive dyskinesia, hyperkinesias, mania, Morbus Parkinson, steel-Richard syndrome, Down's syndrome, myasthenia gravis.

NgR and its ligands may also be involved in the generation or development of inflammatory or autoimmune states involving known inflammatory elements (Teng & Tang, 2005; Fontoura & Steinmann, 2006). These diseases include, but are not limited to rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthropathy, arthropathy, Reiter's disease, psoriatic arthropathy, ulcerative colitic arthropathy, enteropathic synovitis, chlamydia, *yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B. Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma). The human antibodies, and antibody portions of the present application can be used to treat humans suffering from autoimmune diseases, in particular those associated with inflammation, including, rheumatoid spondylitis, allergy, autoimmune diabetes, autoimmune uveitis.

It is also known that NgR interacts with other proteins including but not limited to proteins relevant to cell adhesion, cell migration, cell tracking, axon path finding, and extracellular matrix proteins. A potential therapeutic combination comprised in the present application may include antibodies against NgR and semaphorins (in particular Sema-1a, 1b; Sema-2a; Sema3A, B, C, D, E, F; Sema4A, D; Sema5A; Sema6D; Sema7A; Sema VA), plexins (Plexin-A1-4, Plexin-B1-3, Plexin-C1, Plexin-D1, Tim-2), neuropilins (neuropilin-1 and neuropilin-2), cadherins (E-cadherins and N-cadherins), netrins (netrin-1), ephrins (EphA3, 4, 6, 7, 8; B2, B3) Eph receptors, Eph ligands, Ig CAMs, tenascin-C, CSPGs, tenascin, Sema 3A, fibronectin, laminin-1, collagen (e.g. collagen-IV), Robo, Abl, N-Cadherin, L1, NCAM.

NgR has been described also to interact with the extracellular amyloid precursor protein fragments (AB). Thus, the present application comprises a combination among antibodies against NgR and Aβ species (Aβ 1-40, Aβ 1-42, Aβ oligomers, Aβ multimers, Aβ globulomer). This type of combination therapy may be interesting for the treatment of Alzheimer's disease. The combination may translate into a dual effect on neurite outgrowth/neuroprotection and alleviation of plaque load and cognitive performance in AD patients. Axonal and dendritic loss is a very early hallmark of Alzheimer's disease and a combinatorial treatment may be very efficacious.

Also, as previously discussed, dual-specific antibodies between any one of the partners described above may be of use. Such antibody preparations as described above may be useful for the treatment of Alzheimer's disease, Parkinson's disease, spinal cord injury, traumatic brain injury, multiple sclerosis, peripheral nerve injury, schizophrenia, depression, anxiety, as well as any plasticity and neurite growth and neurotoxicity related disease cited above.

The antibodies of the present application may also be combined with peptides allowing the trans-membrane transfer to include intracellular target proteins. Such peptide sequences may include, but are not limited to, tat, antennapedia, polyargs, some anti-microbial peptides. Such peptides may allow transfer through membranes, including cellular plasma membranes, but also epithelia and endothelial membranes, including the blood-brain-barrier, gut mucosa, meninges, and others.

Such peptides may also allow entry of cell signaling inhibitors into the cells, which may include antibodies or small molecules against NgR signaling molecules, including ROCK, small GTPases, actin and myelin stabilizer.

An antibody, or antibody portion, of the present application also can be administered with one or more additional small molecule therapeutic agents useful in the treatment of disorders in which NgR activity is involved as discussed in the foregoing paragraphs. It should be understood that the antibodies of the present application or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent that affects the viscosity of the composition. Preferred combinations may include, but are not limited to, antipsychotic agents such as, but not limited to Risperidone, Olanzapine, Quetiapine, Phenothiazines (Chlorpromazine, Fluphenazine, Levomepromazine, Pericyanine, Perphenazine, Prochlorperazine, Promazine, Thioridazine, Trifluoperazine), Butyrophenones (Benperidol, Haloperidol), Zotepine, Loxapine, Aripiprazole, Sertoline, Ziprasidone, small molecular inhibitors of Rho kinase activity (ROCK), including compounds like fasudil, dimethylfasudil or any other ROCK inhibitor, small receptor ligands against GABA A receptors or metabotropic glutamate receptors (mGluRs), non-steroidal anti-inflammatory drugs (NSAIDS), anti-inflammatory corticosteroids such as methylprednisolone.

Pharmaceutical Compositions of the Invention

The antibodies and antibody portions of the present application can be incorporated into pharmaceutical compositions suitable for administration to a subject. The pharmaceutical compositions of the present application may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like, that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols (such as mannitol, sorbitol), or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The compositions of the present application may be in a variety of forms. These include, for example, liquid, semisolid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection. Yet another preferred embodiment includes the application of the antibody intrathecally.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies and antibody portions of the present application can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, ed., *Sustained and Controlled Release Drug Delivery Systems*, Marcel Dekker, Inc., New York, 1978.

In certain embodiments, an antibody or antibody portion of the present application may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, bucal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

EXAMPLES

The present application will be further clarified by the following examples, which are only intended to illustrate the present application and not to limit its scope in any way.

Example 1

Production of Antibodies

A/J mice (The Jackson Laboratories, Bar Harbor Me.) were immunized with recombinant human and rat NgR protein (SEQ ID NO:1 and SEQ ID NO:2, respectively. Mice were immunized 4 times subcutaneously with 50 ug recombinant human or rat NgR protein in Complete Freund's adjuvant for the first injection and Immuneasy™ (Qiagen) for the last three immunizations. Four days prior to fusion, mice were injected with 10 ug of antigen intravenously. For the fusion, spleen cells from immunized animals were fused with SP2/0-Ag14 myeloma cells at a ratio of 5:1 using the standard techniques of Kohler and Milstein (Kohler G and Milstein C; Nature Vol. 256, pages 495-497 (1975). Seven to ten days post fusion, when macroscopic hybridoma colonies were observed; supernatants were tested by ELISA assays. Recombinant human or rat NgR protein(s) at 1 ug/ml in PBS were coated on ELISA plates overnight at 4° C. and blocked for one hour at room temperature. Diluted supernatants were incubated and binding was detected with Goat anti-mouse IgFc-HRP conjugate. Hybridoma cells producing antibody positive in the ELISA were scaled up and subcloned by limiting dilution. The isotype of the antibody was determined using the Zymed EIA isotyping kit.

Different ELISA formats have been established and are routinely used as a first screen to identify antibodies that bind to the human, rat or mouse NgR. Antibodies that reacted in the ELISA assays were then tested for binding to HEK or CHO cells that stably expressed recombinant human NgR or recombinant rat NgR, and not their untransfected or control cells. For the ELISA format, the soluble receptors were produced (see above). For the FACS studies, full-length NgR proteins were expressed in recombinant cell lines. Results for Mab 50 SEQ ID NO: 3 and SEQ ID NO:4 and Mab51 SEQ ID NO:5 and SEQ ID NO:6 in ELISA binding and FACS assays are shown in Table 2.

TABLE 2

Summary of binding properties of Mab 50 and Mab 51

| Monoclonal Antibody | ELISA binding HuNgR 6X His (SEQ ID NO: 12) | ELISA Binding Rat NgR 6x His (SEQ ID NO: 12) | FACS binding HEK293 NGR | FACS binding HEK293 Control | FACS binding CHO K1 Rat NGR | FACS binding CHO K1 Control | Isotype |
|---|---|---|---|---|---|---|---|
| Mab 50 | Positive | Positive | Positive | Negative | Positive | Negative | IgG2a, k |
| Mab 51 | Positive | Positive | Positive | Negative | Positive | Negative | IgG2a, k |

Additional antibodies Mab 1, Mab 52, Mab 53, Mab 54, Mab 55, Mab 56, Mab 57, Mab 58, Mab 59, Mab 60, Mab 61, and Mab 62 were obtained using the same experimental protocol.

Example 2

Determining Antibody Specificity and Binding Affinity by ELISA

Figure 1B:
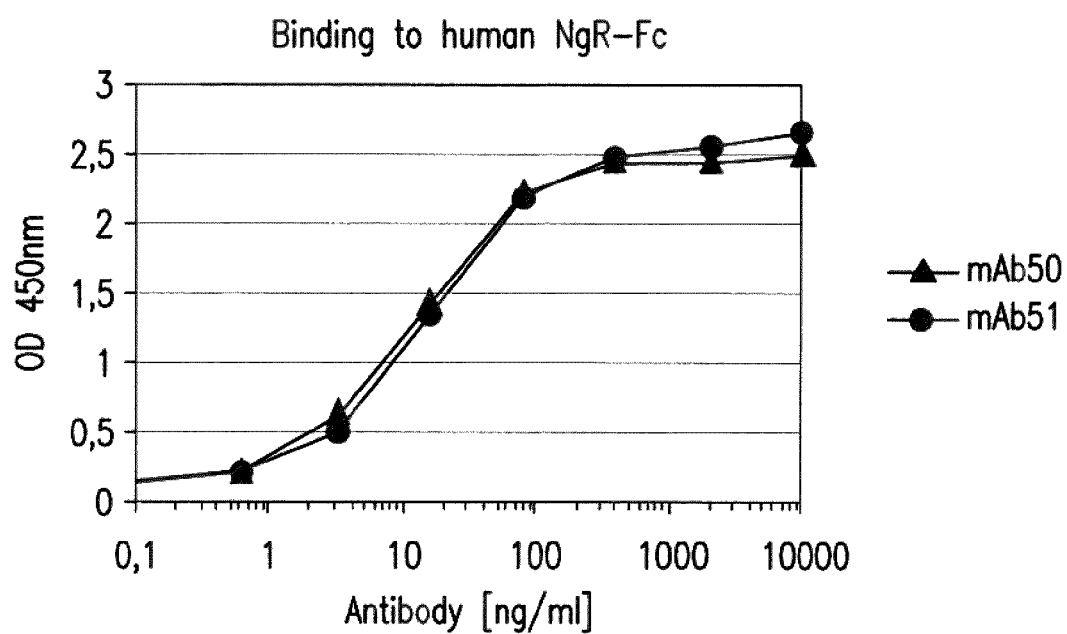

To determine the specificity of the monoclonal antibodies produced in Example 1, an ELISA using NgR-Fc (a fusion protein comprising amino acids Met 1 to Ser 447 of the human NgR and a human Fc fragment (R&D Systems)) and rat NgR (SEQ ID NO. 2), was performed. Both ligands were immobilized on 96-well microtiter plates (Nunc Maxisorb; 0.2 µg/well). As a blocking reagent 2% bovine serum albumin (BSA) in Tris-HCL, pH 7.2 was used for 2 h at room temperature. The monoclonal antibodies were used in concentrations starting at 10,000 ng/ml. Bound antibodies were detected with a secondary anti-mouse antibody labeled with horseradish peroxidase (Sigma) and developed using 3,3',5, 5'-tetramethylbenzidine substrate (TMB, Pierce) under standard conditions. mAb50 and mAb51 specifically bound to human NgR. When using 0.2 µg human NgR-Fc/well a 50% binding was seen for both monoclonal antibodies at concentrations of less then 20 ng/ml (FIG. 1A). In similar experiments, mAb50 and mAb51 also specifically bound to a polypeptide consisting of amino acids of the rat NgR. When using 0.2 µg rat NgR/well of a 96-well microtiter plate a 50% binding was seen for both monoclonal antibodies at concentrations of less then 20 ng/ml (FIG. 1B) The rest of the monoclonal antibodies (mABs) of the present invention also bound to the human and to the rat NgR. Differences in the signals obtained with each antibody suggested differences in binding affinities (See Table 3)

TABLE 3

Summary of EC50 values for mAbs using human or rat NgR

| mAb | EC50 human NgR ng/ml | rat NgR ng/ml |
| --- | --- | --- |
| 1 | 10 | 10 |
| 4 | 8 | >100 |
| 52 | 3 | 4 |
| 53 | 3 | 2 |
| 54 | 5 | 4 |
| 55 | 2 | 10 |
| 56 | 8 | 20 |
| 57 | 20 | >100 |
| 58 | 5 | 15 |
| 59 | 15 | 15 |
| 60 | 2 | 5 |
| 62 | 10 | 7 |

Example 3

Characterization of Antibody Binding to Soluble Human and Rat NgR Using Dot Blots and Western Blots For dot blots, 2 µl protein in different concentration were spotted in TTBS buffer onto dry nitrocellulose membrane. For Western blots filterpaper and nitrocellulose were soaked for 10 min in Novex transfer buffer with 20% methanol. Blotting was achieved in a Novex chamber at constant current (100 mA) for 2 hrs at room temperature.

The amount of protein added per spot was:

| a) 100 µg/ml ≈ | 200 ng/spot |
| --- | --- |
| b) 50 µg/ml ≈ | 100 ng/spot |
| c) 10 µg/ml ≈ | 20 ng/spot |
| d) 5 µg/ml ≈ | 10 ng/spot |
| e) 1 µg/ml ≈ | 2 ng/spot |
| f) 500 ng/ml ≈ | 1 ng/spot |

After spotting the probes, the membrane dried for 10 min at room temperature before starting the immunodetection protocol.

All tested monoclonal antibodies bound to the human and to the rat NgR. Differences between signals obtained with different antibodies suggested differences in binding affinity. (MAB61 did show high background on blots under our conditions used for probing the nitrocellulose membranes.) Binding was antibody dependent since omitting the antibodies directed against the NgR "control" did not show any signal.

The monoclonal antibodies reacted differently to the denatured NgR on Western Blots. Only MAB1 did show prominent signals to the human as well as to the rat NgR. As a control for the binding ability of the antibodies dots containing non-denatured human-NgR and non-denatured rat-NgR were spotted onto the nitrocellulose membrane after the proteins were transferred from the SDS gels. These dots served as positive controls confirming binding of all monoclonal antibodies to the non-denatured proteins on the same nitrocellulose membrane. Results are summarized in Table 4.

TABLE 4

Dot blot and Western blot analyses.

| | Dot Blot | | Western Blot | |
| --- | --- | --- | --- | --- |
| antibody | hNgR | rNgR | hNgR | rNgR |
| MAB1 | +++ | ++ | +++ | ++ |
| MAB52 | +++ | +++ | − | − |
| MAB53 | +++ | ++ | ~ | − |
| MAB54 | ++ | + | − | − |
| MAB55 | +++ | ++ | ~ | − |
| MAB56 | ++ | + | − | − |
| MAB57 | ++ | ~ | − | − |
| MAB58 | ++ | + | − | − |
| MAB59 | +++ | ++ | ~ | − |
| MAB60 | +++ | ++ | ~ | − |
| MAB61 | ++ | + | − | − |
| MAB62 | +++ | ++ | ~ | − |

+++: very strong signal;
++: strong signal;
+: signal;
−: no signal;
~: no relevant signal.

Example 4

Competition of AP-Nogo66 Binding to Soluble Human Nogo Receptor (hNgR-Fc)

To further characterize the monoclonal antibodies a competition assay similar to the binding assay of Example 2 was used to test the ability of the mAbs produced in Example 1 to inhibit AP-Nogo66 binding to human NgR-Fc. Human NgR-Fc (0.2 µg/well) was immobilized on 96-well microtiter plates (Nunc Maxisorb) in 50 mM Na-carbonate buffer pH 9 over night at 4° C. followed by a 2 h blocking step with 2%

Figure 2:
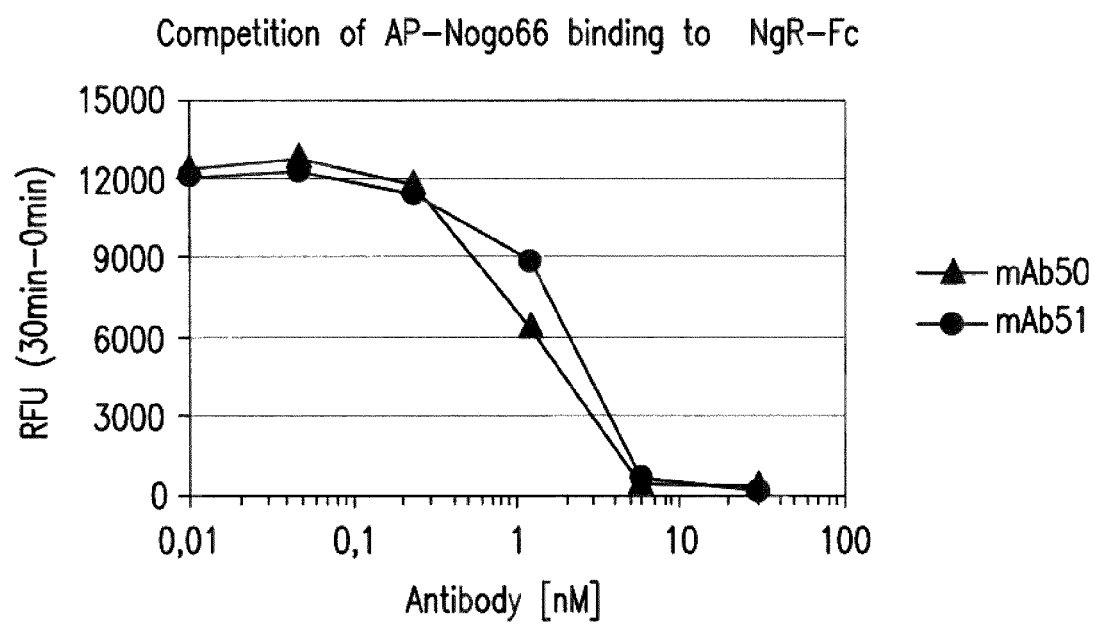
FIG. 2: Competition of AP-Nogo66 binding to NgR-Fc by mAb50 and mAb51.

BSA in Tris-HCL, pH 7.2 at room temperature. The wells received a constant concentration of AP-Nogo66 (final concentration 0.15 nM in Tris-HCL, pH 7.2 with 0.1% BSA) and increasing concentrations of the mAbs. Plates were incubated for 90 min at room temperature. During each incubation step plates were washed with washing buffer (10 mM Tris-HCl, pH7.2 and 0.05% Tween20). Binding of AP-Nogo66 was detected with the AttoPhos substrate (Roche) and the fluorescence units were measured in the Polarstar (BMG) instrument. FIG. 2 shows the relative fluorescence units (RFU) for measurements taken at 0 min and 30 min for mAb 50 and mAb 51. The binding was completely blocked by mAb 50 and mAb 51, and a 10-fold molar excess of both antibodies was required to inhibit 50% of AP-Nogo66 binding to human NgR-Fc. The remaining antibodies, mAb 52, mAb 53, mAb 54, mAb 55, mAb 56, mAb 57, mAb 58, mAb 59, mAb 60, mAb 61, and mAb 62 except mAb1, blocked the binding of AP-Nogo66 to soluble Nogo receptor, in a similar concentration range as seen for mAb 50 and 51.

Example 5

Competition of AP-Nogo66 Binding to Human and Rat NgR on HEK293f Cells by mAB50 and mAb51

Figure 3A:
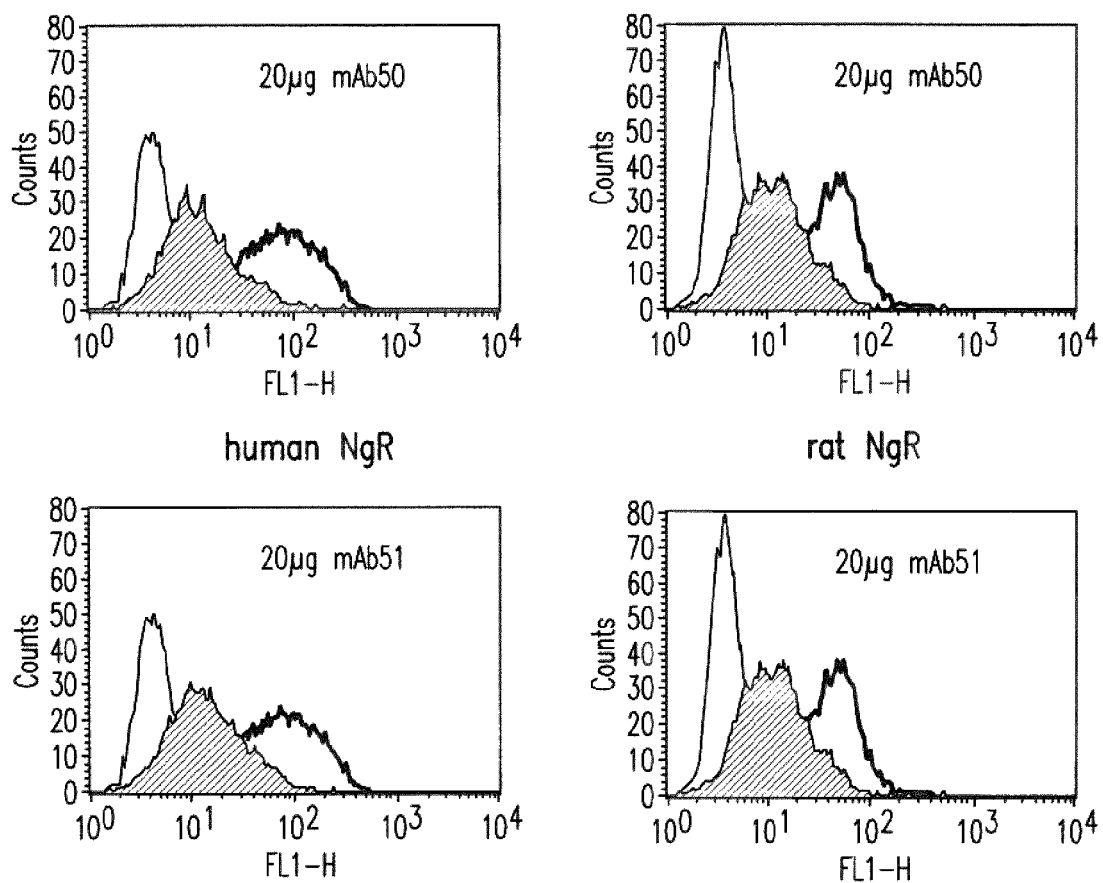
FIG. 3: Competition of Nogo66 binding to human and rat NgR expressed on HEK293f cells by mAB50 and mAB51.

To further characterize the binding and competitive properties of mAbs produced as described in Example 1, a suspension of HEK293f cells transiently expressing human or rat NgR was used. 48 h after transfection the cells were plated in 96-well microtiter plates (Nunc Maxisorb) and washed with Phosphate buffered saline buffer (PBS containing 1% BSA). 1 µg/200 µl of AP-Nogo66 (final concentration 40 nM) and varying concentrations of monoclonal antibodies (20 µg, 4, 0.8 and 0.16 µg/200 µl) were added and incubated for 1 h at 4° C. A monoclonal antibody with the same isotype was used as a negative control. The binding of AP-Nogo66 was detected with an anti-alkaline Phosphatase antibody (Sigma), which was labeled with Alexa Fluor using the Zenon mouse IgG2a labeling kit (Invitrogen). The secondary antibody was incubated for 1 h at 4° C. At the end of the incubation, the cells were washed with PBS and subjected to FACS analysis. At the 20 µg/200 µl concentration (20 fold molar excess) polyclonal anti-NgR antibody and the NgR-Fc (both from R&D Systems) blocked the AP-Nogo66 binding between 60% and 70%, while mAb 50 and 51 blocked the AP-Nogo66 binding by approximately 90%. The antibody isotype control is shown in FIG. 3a for mAb 50 and mAB 51 in rat and human NgR at a concentration of 20 µg. The antibody isotype control is shown as black lines (leftmost signal) and the AP-Nogo66 binding in the absence of any antibody is shown as red lines (rightmost signal). Both human and rat NgR bound AP-Nogo66 equally well. The AP-Nogo66 fluorescence is shifted to lower intensities (shaded; green area) in the presence of both antibodies in HEK293f cells expressing human and rat NgR. Using different antibody concentrations an $IC_{50}$ was seen with a 2-fold molar excess of monoclonal antibodies 50 and 51 versus AP-Nogo66 for both the human and rat NgR as determined by the Kolmogorov-Smirnov (K-S) assay.

Figures 1, 3B:
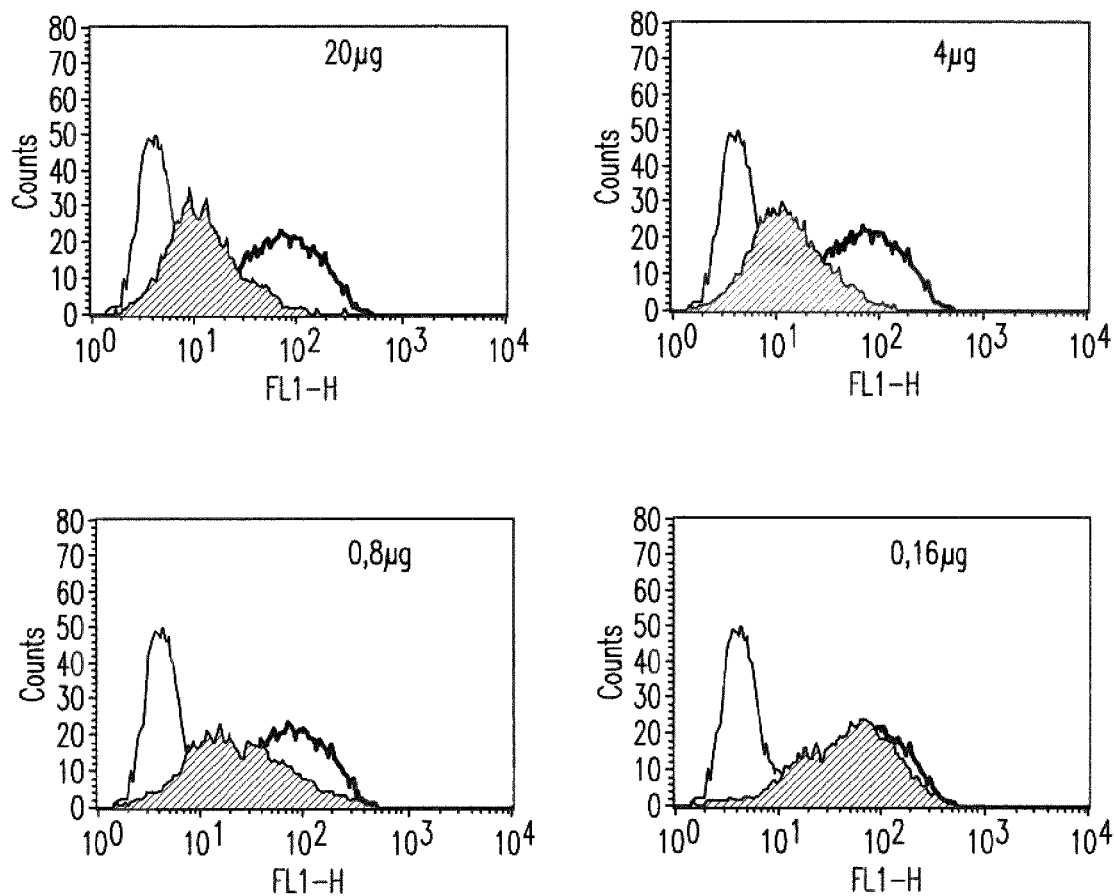
Figures 2, 3B:
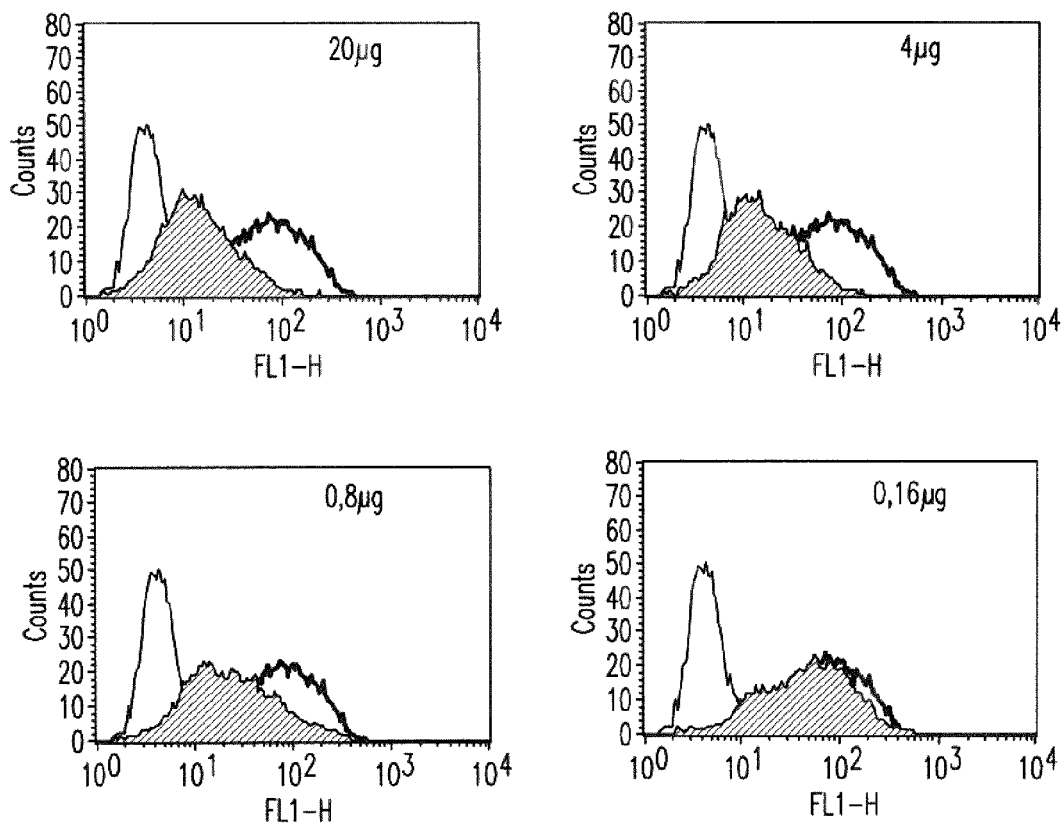

FIG. 3b shows the results with varying concentrations of mAb 50 and mAb 51, i.e. 20.0 µg, 4.0, 0.8 and 0.16 µg/200 µl. The other mAbs of the invention blocked binding of AP-Nogo66 to Nogo receptor expressed on HEK293f cells, in a similar concentration range as seen for mAb 50 and 51. See Table 5, which indicates the amount of antibody required for a 50% competition of AP-Nogo66 binding human NgR expressed on HEK293f cells.

TABLE 5

Competition of AP-Nogo 66 to human and rat HEK293f cells.

| mAb | 50% Competition (µg) |
|-----|---------------------|
| 50 | 0.5 |
| 51 | 0.5 |
| 52 | 3 |
| 53 | 3 |
| 54 | 0.8 |
| 55 | 0.6 |
| 56 | 0.8 |
| 57 | 0.2 |
| 58 | 0.2 |
| 59 | 3 |
| 60 | 0.8 |
| 62 | 0.3 |

Example 6

Neutralization of AP-Nogo66-Induced Neurite Outgrowth Inhibition by mAB50 and mAb51 in NTera2 Cells Antibodies of the present invention were studied for their effects on neurite outgrowth in a functional system closely resembling the in vivo situation using human NTera-2 cells and rodent (mouse cortical neurons, rat cortical neurons and rat cerebellar granule neurons) cell types, and AP-Nogo66 and myelin as ligands.

Figure 4:
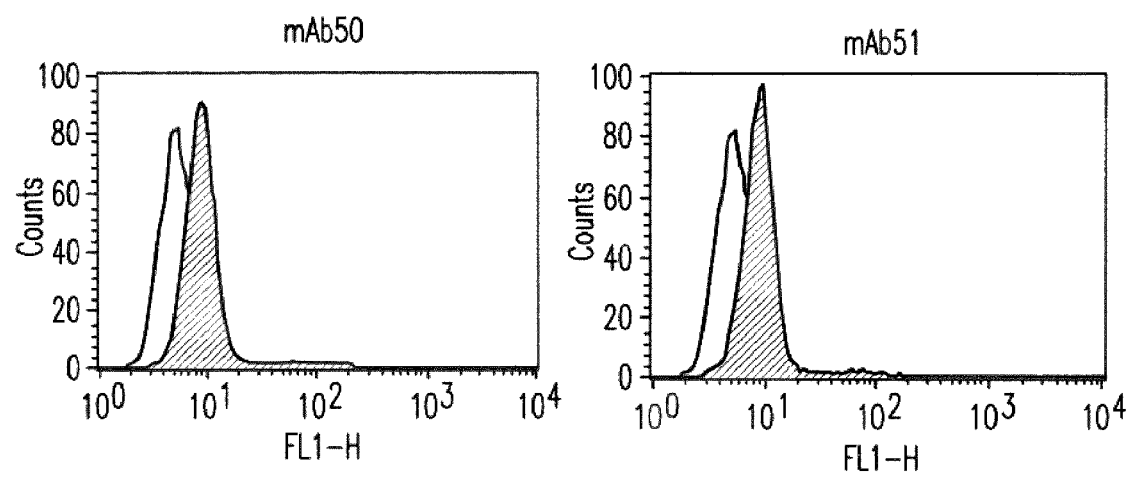
FIG. 4: Binding of mAB50 and mAB51 to NTera 2 cells.

NTera2 cells (a human teratocarcinoma cell line) can be differentiated into neuron-like cells using retinoic acid, that express NgR mRNA (PCR) and cell surface protein as shown by modest binding of a polyclonal antibody to NgR (FACS binding). The expression of the natural human NgR by NTera-2 cells on the cell surface was detected by FACS analysis using an isotype control antibody (unshaded area) and mAb 50 and mAb 51 (shaded area), respectively (FIG. 4). The binding of both antibodies to the NgR expressed on the surface of the Ntera-2 cells is shown by the shaded areas.

Analysis of neurite outgrowth or growth cone collapse in these differentiated cells is an in vitro system as close as possible to the human neuron. NTera2 cells (from the German National Resource Center for Biologicals, DMSZ, Braunschweig) were thawed and plated in 175 cm² culture flasks (Greiner bio-one #660175) with DMEM medium (Gibco #31966-021+10% fetal calf serum (FCS)+5% Horse Serum (PS)). After several days in culture the cells were replated. For this the cells were washed once with PBS (Gibco #14190-094), washed with trypsin/EDTA (Gibco #25300-054) and incubated with trypsin/EDTA for 5 minutes. For differentiation, the cells were resuspended, 2.5×10⁶ cells were plated on 175 cm² flasks in DMEM (Gibco 31966-021, Lot. Nr. 3092594) plus 10% FCS+5% PS, plus 1% Penicillin/Streptomycin (5000/5000 units/mL), plus retinoic acid (SIGMA #R2625) at a final concentration of 10 µM).

For differentiation, retinoic acid (SIGMA #R2625) at a final concentration of 10 µM was added twice-weekly to the NTera2 cells over a period of three weeks. After 21 days differentiation the cells were replated. For this the cells were washed once with PBS, washed with trypsin/EDTA and incubated with trypsin/EDTA for 5 minutes. The cells were resuspended, split 1:6 and plated on six 175 cm² flasks in DMEM (Gibco 31966-021, Lot. Nr. 3092594)+10% FCS+5% PS+1% PenStrep) for 2-3 days.

After 2-3 days cells were washed with PBS, physically detached, centrifuged for 5 minutes at 1000 rpm, resuspended in Neurobasal medium (Gibco #21103-049) plus 2 mM L-Glutamine (Gibco #25030-024) plus Penicillin/Streptomycin plus B27-Supplement) and pre-aggregated in an Erlenmeyer flask (Corning #431143). Thereby $10^6$ cells/mL were added to 2×15 mL aggregation medium (Neurobsalmedium (Gibco #21103-049) plus 2 mM L-Glutamine (Gibco #25030-024) plus Penicillin/Streptomycin plus B27-Supplement)), gently agitated over night at 37° C., 5% $CO_2$ and plated on 96 well plates (Biocoat Poly-D-Lysin Cellware 96-Well Black/Clear Plate Becton Dickinson #35 4640 (35 6640)) pre-coated with inhibitory and control substrates. For the inhibitory substrates half of the 96 well plate was pre-coated with 100 µL AP-Nogo66 (concentration AP-Nogo66 was 15 µg/mL) plus Laminin (Sigma, L-2020, Lot 014K4060, (stock solution. 1 mg/mL)) in sterile PBS; final amount of Laminin per well 20 µg. For the permissive substrate the second half of the plate was coated with 100 µl Laminin (20 µg). After an incubation of 2 hours the plates were washed twice with PBS and 50 µl of the pre-aggregated cell suspension were plated in each well, supplemented with 40 µl of medium. Plates were incubated at 37° C. for 2 hours, and finally 10 µl of pre-diluted mAb 50 or mAb 51 solution was added to give a final antibody concentration between 1 and 100 µg/mL. Cells were incubated over night at 37° C., 5% $CO_2$, the following day fixed with 2% paraformaldehyde (SIGMA #P-6148) and stored at 4° C. for subsequent analysis. The analysis of neurite outgrowth was performed with software AxioVision LE Rel. 4.1, whereby the standard evaluation parameters were used (aggregate area and aggregate area & neurite growth area).

Figure 5:
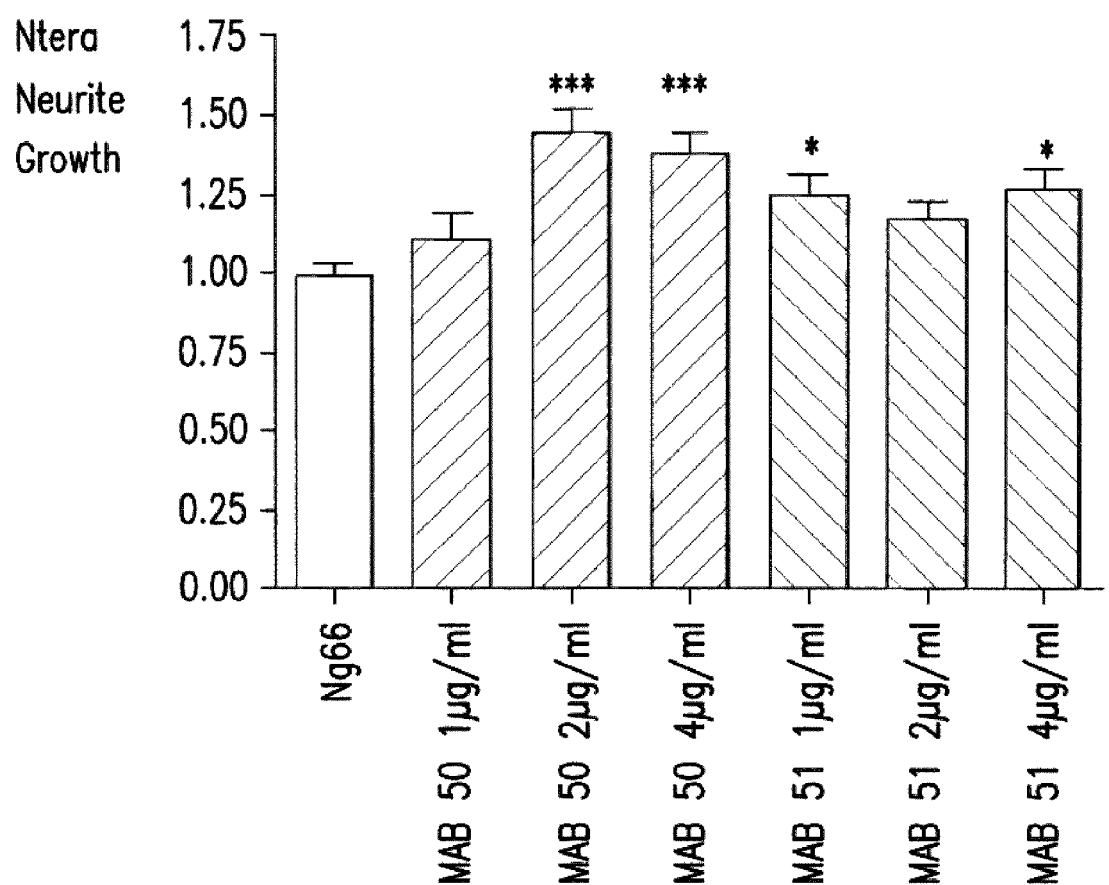
FIG. 5: Quantification of neurite outgrowth from NTera 2 cell aggregates.

Neurite outgrowth from NTera2 aggregates was quantified with the method described above. Results are shown in FIG. 5, significant amelioration of neurite outgrowth can be observed at 2 µg/ml for mAb50 and at 1 µg/ml for mAb51. Significance versus Nogo66 treatment: *=p-value<0.05; ***=p-value<0.00.1

Amelioration of neurite outgrowth inhibition was also obtained for antibodies Mab52, 53, 54, 55, 56, 57, 58, 59, 60, 61 and 62. Mab1 and Mab4 did not ameliorate the inhibition of neurite outgrowth by AP-Nogo66.

Example 7

Deletion Mutants of the hNgR: Expression, Purification and Binding of Antibodies hNgR was expressed as soluble protein by deletion of C-terminal amino acids to prevent GPI-linker formation (450 last amino acid) and membrane attachment and by using a secretion signal to potentially increase the amount of secreted protein. The expression system used was based on transient transfection of expression plasmids in 293F cells. His-tagged secreted proteins were captured by using Ni-NTA (Nickel-nitrilotriacetic acid) beads. Eluted proteins were analyzed for purity and size by PAGE and Western Blot using a his-tagged unrelated protein (RGM A-His) as a negative control. To better adjust for NgR-protein in these preparations, the amount of NgR was measured by dot blots using a polyclonal antibody (AF1208) to the hNgR expected to detect all deletion mutants. Dot blots using the adjusted amount of protein for the different NgR deletion mutants were performed. Dot blots were used for immunodetection with the listed antibodies. Binding of antibodies to the NgR-deletion mutants was further characterized using cell culture supernatants of 293F-cells expressing NgR deletion mutants as a source of non-purified NgR (i) Generation of NgR-deletion mutants according to Fournier et al. (Truncated Soluble Nogo Receptor Binds Nogo-66 and Blocks Inhibition of Axon Growth by Myelin; Alyson E. Fournier, Graham C. Gould, Betty P. Liu, Stephen M. Strittmatter; The Journal of Neuroscience, Oct. 15, 2002, 22(20):8876-8883). Seven (7) deletion mutants of the human NgR have been described in the literature (Fournier et al.). The seven mutant constructs were generated from pSecTag2A IgK/hNgR 27-450/Myc/His. This construct contains the coding region for amino acids 27-450 of the human NgR fused to an IgK leader peptide and a C-terminal Myc- and His tag in a pSecTag2A vector. The following constructs were generated:

pSecTag2AigK/hNgR 27-450/Myc/H is
pSecTag2AigK/hNgR 58-450/Myc/His
pSecTag2AigK/hNgR27-450/Δ58-106/Myc/His
pSecTag2AigK/hNgR27-450/Δ106-155/Myc/His
pSecTag2AigK/hNgR27-450/Δ155-202/Myc/His
pSecTag2AigK/hNgR27-450/Δ203-250/Myc/His
pSecTag2AigK/hNgR27-450/Δ260-310/Myc/His
pSecTag2AigK/hNgR 27-310/Myc/His

All constructs except pSecTag2AigK/27-310/Myc/His were generated using the QuikChange II XL Site Directed Mutagenesis Kit (Stratagene, #200521) and transformations were performed in *E. coli* XL10 Gold cells. For pSecTag2AigK/NgR/27-310/Myc/His the according region of the coding sequence was amplified and cloned into pSecTag2A. The following mutagenesis and amplification primers were used for deleting the different parts of the NgR coding region.

```
1. pSecTag2AigK/hNgR 58-450/Myc/His
Mey 1008: sense primer
GCCAGGCGCGCCGTACGAAGCTTATGCGCCAGCCAGCGCATCTTCCTGC

ACGGC (SEQ ID NO: 13)

vector sequence
hNgR sequence starting with amino acid A58

Mey 1009: antisense primer
GCCGTGCAGGAAGATGCGCTGGCTGGCGCATAAGCTTCGTACGGCGCGC

CTGGC (SEQ ID NO: 14)

vector sequence
hNgR sequence starting with amino acid A58

2. pSecTag2AigK/hNgR27-450/Δ 58-106/Myc/His
Mey 1014: sense primer
GCTGTGCCCGTGGGCATCCCTGCTGCCCTCCTGGAGCAGCTGGACCTCAG

CGATAATGC (SEQ ID NO: 15)

hNgR sequence up to amino acid A58
hNgR sequence starting from amino acid L106

Mey 1015: antisense primer
GCATTATCGCTGAGGTCCAGCTGCTCCAGGAGGGCAGCAGGGATGCCCAC

GGGCACAGC (SEQ ID NO: 16)

hNgR sequence up to amino acid A58
hNgR Sequenz starting from amino acid L106

3. pSecTag2AigK/hNgR27-450/Δ 106-154/Myc/His
Mey 1021: sense primer
GCGGCTGCCTTCACTGGCCTGGCCGCCCTGCAGTACCTCTACCTGCAGGA

CAACGC (SEQ ID NO: 17)

hNgR sequence up to amino acid A105
hNgR sequence starting from amino acid A155
```

-continued

Mey 1022: antisense primer
GCGTTGTCCTGCAGGTAGAGGTACTGCAGGGCGGCCAGGCCAGTGAAGGC

AGCCGC (SEQ ID NO: 18)

hNgR sequence up to amino acid A105
hNgR Sequence starting from amino acid A155

4. pSecTag2AigK/hNgR27-450/Δ 155-202/Myc/His
Mey 1023: sense primer
CGGGGCTGTTCCGCGGCCTGGCTAGCCTCGACCGTCTCCTACTGCACCAG

AACCGC (SEQ ID NO: 19)

hNgR sequence up to amino acid A154
hNgR sequence starting from amino acid S203

Mey 1024: antisense primer
GCGGTTCTGGTGCAGTAGGAGACGGTCGAGGCTAGCCAGGCCGCGGAACA
(SEQ ID NO: 20)

hNgR sequence up to amino acid A154
hNgR Sequence starting from amino acid S203

5. pSecTag2AigK/hNgR27-450/Δ 203-250/Myc/His
Mey 1025: sense primer
GAGCGCGCCTTCCGTGGGCTGCACGCCCTGCAGTACCTGAGGCTCAACG

ACAACC (SEQ ID NO: 21)

hNgR sequence up to amino acid H202
hNgR sequence starting from amino acid A251

Mey 1026: antisense primer
GGTTGTCGTTGAGCCTCAGGTACTGCAGGGCGTGCAGCCCACGGAAGGC

GCGCTC (SEQ ID NO: 22)

hNgR sequence up to amino acid H202
hNgR Sequence starting from amino acid A251

6. pSecTag2AigK/hNgR27-450/Δ 260-310/Myc/His
Mey 1027: sense primer
GCGTGCCCTGCAGTACCTGAGGCTCAACGACGTGGCCACCGGCCCTTACC

ATCCCATCTG (SEQ ID NO: 23)

hNgR sequence up to amino acid D259
hNgR sequence starting from amino acid V311

Mey 1028: antisense primer
CAGATGGGATGGTAAGGGCCGGTGGCCACGTCGTTGAGCCTCAGGTACTG

CA (SEQ ID NO: 24)

hNgR sequence up to amino acid D259
hNgR Sequence starting from amino acid V311

7. pSecTag2AigK/hNgR27-310/Myc/His
Mey 1016: sense primer
CCCCAAGCTTATGCCCAGGTGCCTGC (SEQ ID NO: 25)

hNgR sequence starting from amino acid C27

Mey 1030: antisense primer
CCCCGAATTCCAGCGCAGCCCTGCAGGTC (SEQ ID NO: 26)

hNgR sequence up to amino acid A310

Figure 6:
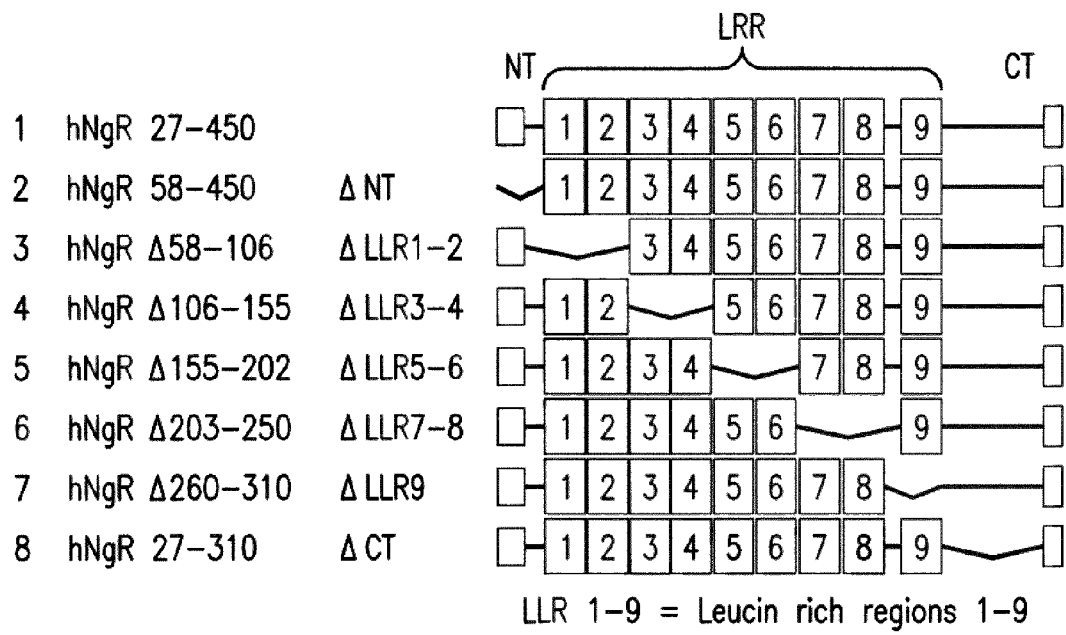
FIG. 6: Deletion mutants of the hNgR.

See a schematic representation in FIG. 6.

(ii) Expression of NgR-deletion mutants.

Deletion of C-terminal amino acids in the human NgR leads to loss of membrane anchor properties and presence of a soluble receptor protein in the cell supernatant. At the N-terminus the signal peptide of the hNgR (amino acids 1-27) was replaced by the signal peptide encoded in the vector. Therefore a N-terminal and C-terminal deletion variant starting at amino acid 27 of the hNgR and ending at amino acid 450 of the hNgR (hNgR27-450) was used as a basis for all these mutants to enable the presence of soluble proteins in the cell supernatants. Additionally these mutants did contain a short amino acid tag to enable purification of these proteins. The DNA of the hNgR mutants were transiently expressed in 293F cells. Cell supernatants were harvested by centrifugation after 72 hrs. Protein purifications were done by methods below. Transfections were done with the following DNA coding for the 7 different mutants of the human NgR.

pSecTag2AigK/hNgR 27-450/Myc/His
pSecTag2AigK/hNgR 58-450/Myc/His
pSecTag2AigK/hNgR27-450/Δ58-106/Myc/His
pSecTag2AigK/hNgR27-450/Δ106-155/Myc/His
pSecTag2AigK/hNgR27-450/Δ155-202/Myc/His
pSecTag2AigK/hNgR27-450/Δ203-250/Myc/His
pSecTag2AigK/h Ng R27-450/Δ260-310/Myc/His
pSecTag2AigK/hNgR 27-310/Myc/His

The DNA of the hNgR mutants were transiently expressed in 293F cells.

(iii) Purification of NgR proteins using Ni-Chelate affinity (Ni-NTA)

Ni-NTA superflow beads (Qiagen Qiagen #1018611) were used. Beads were washed 3 times in PBS (phosphate buffered saline, Invitrogen) by centrifugation of bead suspension at 13500 rpm, discarding the supernatants, resuspending the beads in fresh PBS. 200 μl of bead suspension were used for 30 ml cell culture supernatant. Beads were incubated with cell culture supernatants overnight at 4° C. on a rotator, 60 rpm) and were centrifuged after the incubation (10 min, 3000 rpm) to pellet the beads. Supernatant was discarded and the beads washed 3 times with PBS. Bound proteins were eluted from the beads using 250 μl elution buffer (PBS, 160 mM NaCl, 150 mM Imidazol). After 30 min incubation on a rotator at room temperature beads were pelleted by centrifugation at 13.500 rpm for 3 min. Supernatant was taken. The eluted protein was frozen at −20° C. for further analysis.

The data from dot blot experiments with deletion mutants of the hNgR are summarized in table 6.

TABLE 6

| Antibodies | Mutants | | | | | | | |
|---|---|---|---|---|---|---|---|---|
| | 1 | 2 | 3 | 4 | 5 | 6 | 7 | 8 |
| AF1208 | +++ | +++ | +++ | +++ | ++ | +++ | +++ | ++ |
| MAB1 | +++ | +++ | +++ | +++ | +++ | +++ | +++ | ~ |
| MAB4 | +++ | +++ | +++ | +++ | +++ | +++ | +++ | ~ |
| MAB50 | ++ | − | − | − | − | +++ | − | ~ |
| MAB51 | ++ | − | − | − | − | +++ | − | ~ |
| MAB52 | ++ | − | − | − | − | +++ | − | ++ |
| MAB53 | ++ | − | − | − | − | +++ | − | ++ |
| MAB54 | + | − | − | − | − | + | − | ~ |
| MAB55 | + | − | − | − | − | + | − | ~ |
| MAB57 | ~ | − | − | − | − | − | − | − |
| MAB58 | ++ | − | − | − | ~ | ++ | − | ~ |
| MAB59 | ++ | − | − | − | ~ | ++ | − | ~ |
| MAB60 | +++ | − | − | − | ~ | ++ | − | + |
| MAB61 | + | − | − | − | − | + | − | + |
| MAB62 | + | − | − | ~ | − | + | − | ~ |

+++: very strong signal;
++: strong signal;
+: signal;
−: no signal;
~: no relevant signal.

Example 8A

Competition of MAG-Fc Binding to NgR-Fc

To further characterize the monoclonal antibodies a competition assay similar to the binding assay of Example 2 was used to test the ability of two mAbs produced in Example 1 to inhibit MAG-Fc binding to human NgR-Fc. We immobilized NgR-Fc (0.2 µg/well, R&D Systems) on 96-well microtiter plates (Nunc Maxisorb) in 50 mM Na-carbonate buffer pH 9 over night at 4° C. followed by a 2 h blocking step with 2% BSA in Tris-HCL, pH 7.2 at room temperature.

Figure 7:
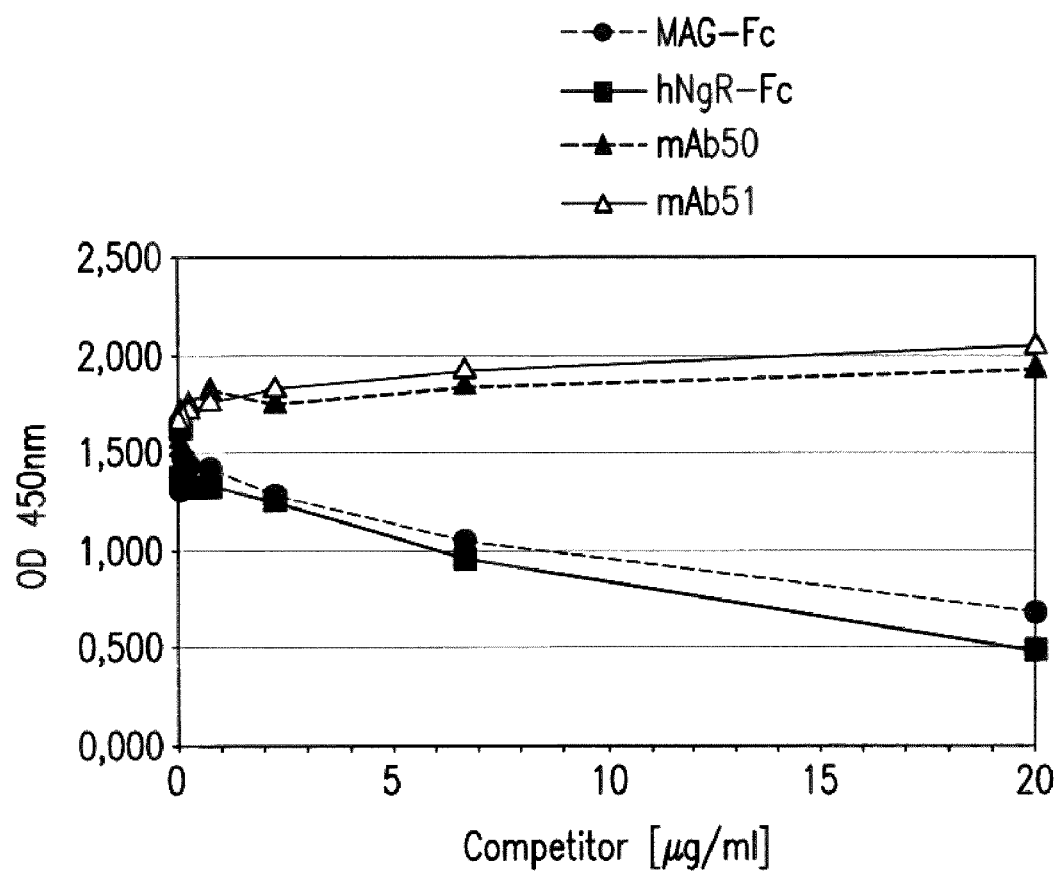
FIG. 7: Competition of MAG-Fc binding to NgR-Fc.

MAG-Fc (R&D Systems recombinant Rat MAG/Fc Chimera, Catalog #538-MG) was labeled with horseradish peroxidase by the Zenon human IgG labeling kit (Molecular Probes). The wells received a constant concentration of labeled MAG-Fc (final concentration 50 ng/ml in Tris-HCL, pH 7.2 with 0.1% BSA) and the indicated concentrations of mAb 50 and mAb 51. This was incubated for 60 min at room temperature and using unlabeled MAG-Fc and NgR-Fc as controls. During each incubation step plates were washed with washing buffer (10 mM Tris-HCl, pH 7.2 and 0.05% Tween 20). Labeled MAG-Fc was developed using 3,3',5,5'-tetramethylbenzidine substrate (TMB, Pierce) under standard conditions. As shown in FIG. 7, mAb 50 (closed triangles) and mAb51 (open triangles) did not inhibit the binding of MAG-Fc to human NgR. MAG-Fc and NgR-Fc competed for the binding of labeled MAG-Fc (closed circles) to human NgR-Fc (a fusion protein comprising amino acids Met 1 to Ser 447 of the human NgR and a human Fc fragment (R&D Systems); closed squares). Therefore, mAb 50 and mAb 51 did not compete with MAG for binding to NgR under these conditions (FIG. 7). None of the other remaining antibodies compete with MAG for binding to NgR under these conditions.

Example 8B

Competition of OMgp Binding to NgR-Fc

To further characterize the monoclonal antibodies a competition assay similar to the binding assay of Example 8a was used to test the ability of two mAbs produced in Example 1 to inhibit oMgp binding to human NgR-Fc. NgR-Fc (0.2 µg/well, R&D Systems) was immobilized on 96-well microtiter plates (Nunc Maxisorb) in 50 mM Na-carbonate buffer pH 9 over night at 4° C. followed by a 2 h blocking step with 2% BSA in Tris-HCL, pH 7.2 at room temperature. The wells received a constant concentration of human OMgp (R&D Systems/1673-OM; final concentration 500 ng/ml in Tris-HCL, pH 7.2 with 0.1% BSA) and the indicated concentrations of mAb 50 and mAb 51. This mixture was incubated for 60 min at room temperature. OMgp binding was detected with anti-His-antibody labeled with horseradish peroxidase (Roche). During each incubation step plates were washed with washing buffer (10 mM Tris-HCl, pH 7.2 and 0.05% Tween 20). Labeled anti-His antibody was developed using 3,3',5,5'-tetramethylbenzidine substrate (TMB, Pierce) under standard conditions.

As shown in Table 7, mAb 50 and mAb51 partially blocked the binding of OMgp to human NgR (30-40% range). The other antibodies, except mAb52 and mAb59, also partially blocked the binding of OMgp to human NgR, even at concentrations up to 80 µg/ml which is more than a 100 fold molar excess (Table 7).

TABLE 7

| mAb | Maximal Competition (%) |
|---|---|
| 1 | 26 |
| 4 | 9 |
| 50 | 33 |

TABLE 7-continued

| mAb | Maximal Competition (%) |
|---|---|
| 51 | 36 |
| 52 | 0 |
| 53 | 27 |
| 54 | 23 |
| 55 | 35 |
| 56 | 37 |
| 57 | 17 |
| 58 | 32 |
| 59 | 0 |
| 60 | 5 |
| 62 | 22 |

Example 9

Neutralization of AP-Nogo66-Induced Neurite Outgrowth Inhibition by mAB50 and mAb51 in Rat DRG Cells Dorsal root ganglions (DRGs) from rat pups of postnatal day 3-6 were used to investigate the action of anti-NgR antibodies on neurite outgrowth.

Figure 8:
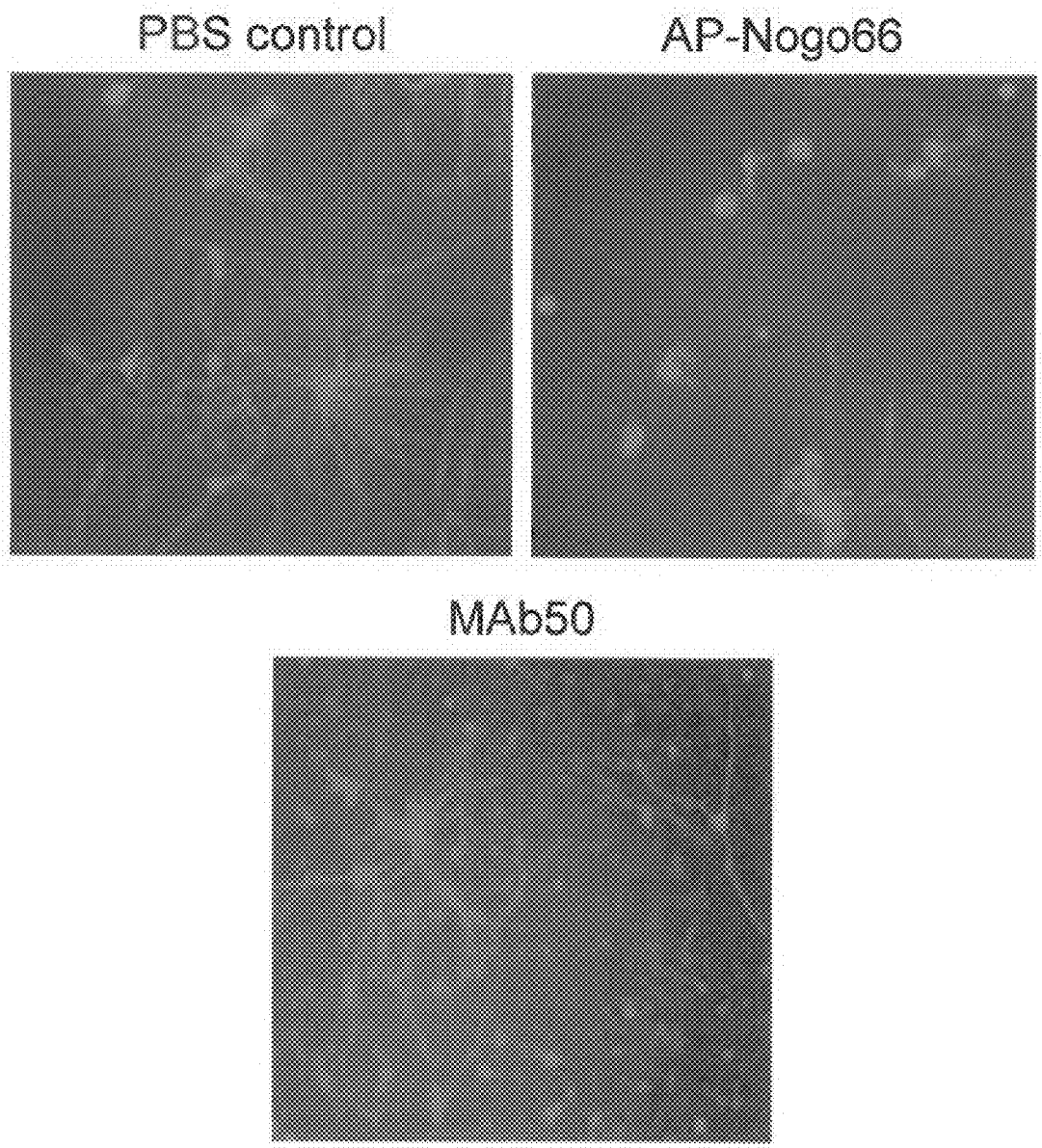
FIG. 8: Rat dorsal root ganglion neurons under permissive and inhibitory conditions and neutralization of Nogo66-induced neurite outgrowth inhibition by mAb50.
Figure 9:
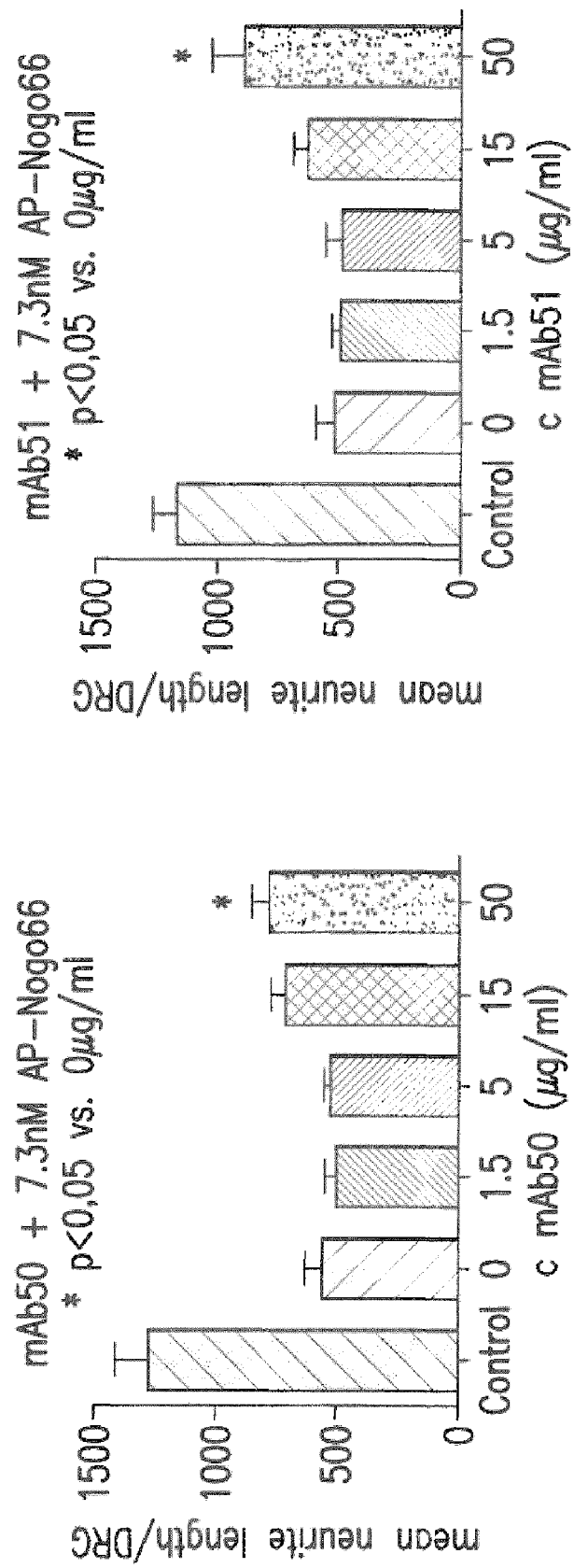
FIG. 9: Neutralization of Nogo66-induced neurite outgrowth inhibition by mAB50 and mAb51 in rat DRG cells.

For the generation of DRGs, 6-8 rat pups were decapitated with a surgical scissor. The vertebral column was dissected from the ventral side by removing ventral organs and the vertebrae. Then, the vertebral column was opened longitudinally with the help of fine scissors. The spinal cords were removed together with the adhering DRGs and were transferred to a 10 cm petri dish containing PBS. DRGs were dissected free from the spinal cord and the connecting nerve fibers by using two fine forceps and were transferred to a 35 mm Petri dish containing 1 ml PBS. After collecting all DRGs, 0.5 ml of collagenase solution (4 mg/ml collagenase Type I, Worthington #CLS-1) in PBS was added and the DRGs were incubated for 20-30 min at 37° C. 0.5 ml of trypsin solution (0.5% trypsin (SERVA #37290) in PBS) was added and the DRGs were incubated for another 15-25 min at 37° C. The DRGs were transferred to a 15 ml tube and 10 ml of medium (DMEM Nut Mix F12 (Gibco #31330-038), plus 5% FCS (Gibco, heat inactivated) plus 5% horse serum (Sigma, heat inactivated) plus 1% penicillin/streptomycine (Gibco #15140-122)) was added. After settlement of the DRGs to the bottom of the tube, the supernatant was removed. DRGs were dissociated in 2 ml medium by 3-5 passages through a Pasteur pipette followed by 2-3 additional passages through a Pasteur pipette with a reduced opening. After settling of cell clumps, the supernatant containing dissociated cells was transferred to a new tube. Cells were collected by centrifugation for 5 min at 1000 rpm, resuspended in 2 ml medium, counted, and diluted to the desired cell density in medium supplemented with Nerve Growth factor (NGF; 62.5 µg/ml final concentration, Roche #1014331). 4000-7000 cells were plated in a volume of 80 µl per well of a poly-lysine coated 96 well plate (e.g. Beckton Dickinson #356640), which had been additionally coated with 100 µl coating solution (1 vial of laminin (1 mg/ml Sigma #L-2020) diluted with 50 ml of sterile water), followed by a 30 min to 3 h incubation period at 37° C. Cell plating was followed by the addition of increasing concentrations of antibody in a volume of 10 µl. After incubation for 2 h in a $CO_2$ incubator at 37° C. 10 µl of AP-Nogo66 was added. Cells were grown for 18-30 h and fixed by the addition of 100 µl 4% paraformaldehyde solution in PBS (phosphate-buffered saline; Gibco #14190-094), followed by incubation at 4° C. for at least 12 h. As an alternative to 96 well plates, 24 well plates (e.g. Falcon #353047) were used in conjunction with poly-lysine coated coverslips (e.g. Becton Dickinson #354085) and were coated by applying 500 µl coating solution. Neurite outgrowth was visualized by indirect immunofluorescence using an anti-βIII tubulin antibody (e.g. Abcam #ab14545) in conjunction with a Cy3-conjugated 2nd antibody (e.g. Jackson ImmunoResearch #715-165-151). Nuclei were stained by addition of Bisbenzimide (H33258) to the 2nd antibody. Microscopic pictures were taken at 10× magnification on a BDTM Pathway Bioimager (Beckton Dickinson) and neurite length was determined using the AttoNO (Beckton Dickinson) software. Neurite outgrowth was normalized to the number of DRG per picture. FIG. 8 shows the neutralization of AP-Nogo66-induced neurite outgrowth inhibition with mAb50 as an example. FIG. 9 shows the results of an experiment using the antibodies mAb 50 and mAb 51, respectively. Application of AP-Nogo66 strongly reduces the length of neurite outgrowth (2nd columns) compared to control conditions without AP-Nogo66 (1st columns). Both antibodies neutralized the AP-Nogo66 induced inhibition of neurite outgrowth in a dose-dependent fashion. Neurite length normalized to the number of DRG becomes statistically different at 50 µg/ml (last columns) for both antibodies compared to AP-Nogo66 application without the antibodies (2nd columns).

Amelioration of neurite outgrowth inhibition was also obtained for antibodies Mab52, 53, 54, 55, 56, 57, 58, 59, 60, 61 and 62. Mab1 and Mab4 did not ameliorate the inhibition of neurite outgrowth by AP-Nogo66.

From these results it can be concluded that such antibodies have the potential to stimulate neurite growth in a growth-inhibitory environment.

What is claimed is:

1. An isolated antibody, or fragment thereof, that specifically interacts with at least one epitope of a Nogo-66 receptor, wherein the antibody, or fragment thereof, has at least 90% amino acid sequence identity with a sequence selected from the group consisting of a sequence comprising a heavy chain variable region (VH region) comprising SEQ ID NO:3; a sequence comprising a light chain variable region (VL region) comprising SEQ ID NO:4; a sequence comprising a heavy chain variable region (VH region) comprising SEQ ID NO:5; and a sequence comprising a light chain variable region (VL region) comprising SEQ ID NO:6.

2. The antibody or antigen-binding fragment thereof according to claim 1, having at least one characteristic selected from the group consisting of:
   (a) binding to mammalian NgR with affinity in the nM range or less;
   (b) functionally antagonizing in vitro Nogo-66 binding in neurite outgrowth assay with nM or less efficacy;
   (c) in vivo inducing sprouting in the optic nerve crush model; or
   (d) relieving in vivo experimental spinal cord injury.

3. The antibody, or fragment thereof, according to claim 1 wherein said antigen binding fragment comprises a VH and a VL domain.

4. The antibody or fragment thereof according to claim 3 wherein the antibody diminishes the ability of Nogo-66 to bind to its receptor.

5. The antibody or fragment thereof according to claim 3 wherein the antibody is capable of neutralizing Nogo-66.

6. The antibody or fragment thereof according to claim 3 wherein the Nogo66 receptor is selected from human and rat.

7. The antibody or fragment thereof according to claim 3 wherein the Nogo66 receptor polypeptide shares 90% homology to the amino acid sequence selected from SEQ ID NO:1 and SEQ ID NO:2.

8. The antibody or fragment thereof according to claim 3 wherein the Nogo66 receptor is encoded by a nucleic acid that shares 90% homology to the nucleic acid sequence SEQ ID NO:8 and SEQ ID NO:9.

9. The antibody or fragment thereof according to claim 3 wherein the dissociation constant ($K_d$) ranges from $10^{-7}$ to $10^{-13}$ M.

10. The antibody or fragment thereof according to claim 3 has an on rate constant ($K_{on}$) ranging from $10^3$ $M^{-1}$ $s^{-1}$ to $10^7 M^{-1}$ $s^{-1}$.

11. The antibody or fragment thereof according to claim 3 that has an off rate ($K_{off}$) ranging from $10^{-3}$ $s^{-1}$ to about $10^{-6}$ $s^{-1}$.

12. The antibody or fragment thereof according to claim 3 that has an $IC_{50}$ value ranging from $10^{-6}$ $s^{-1}$ to about $10^{-12}$ $s^{-1}$.

13. The antibody or fragment thereof according to claim 3 that binds to human NgR with an $EC_{50}$ ranging from $1 \times 10^{-9}$M to $1 \times 10^{-11}$ M.

14. The antibody or fragment thereof according to claim 3 that binds to human NgR wherein the antibody is glycosylated.

15. The antibody or antigen-binding fragment of claim 3, wherein said antibody or antigen-binding fragment is a mouse antibody, a humanized antibody, a fully human, a chimeric antibody, an antigen-binding fragment of a humanized antibody, or an antigen-binding fragment of a chimeric antibody.

16. The antibody or antigen-binding fragment of claim 3, wherein said antibody or antigen-binding fragment is an antigen-binding fragment selected from the group consisting of a Fab fragment, a Fab' fragment, a F(ab')$_2$ fragment and a Fv fragment.

17. A pharmaceutical composition comprising the monoclonal antibody or antigen-binding portion according to any of claims 3 to 5 and a pharmaceutically acceptable carrier.

18. A monoclonal antibody that specifically binds to at least one epitope of a Nogo-66 receptor, wherein said monoclonal antibody is the monoclonal antibody secreted by hybridoma cell line ATCC NO. PTA-8383.

19. The monoclonal antibody of claim 18, wherein the binding results in inactivation of the Nogo-66 receptor.

20. A monoclonal antibody that specifically binds to at least one epitope of a Nogo-66 receptor, wherein said monoclonal antibody is the monoclonal antibody secreted by hybridoma cell line ATCC NO. PTA-8384.

21. The monoclonal antibody of claim 20, wherein the binding results in inactivation of the Nogo-66 receptor.

* * * * *

SEQUENCE LISTING

```
<160> NUMBER OF SEQ ID NOS: 26

<210> SEQ ID NO 1
<211> LENGTH: 495
<212> TYPE: PRT
<213> ORGANISM: Homo sapiens

<400> SEQUENCE: 1

Met Glu Thr Asp Thr Leu Leu Leu Trp Val Leu Leu Leu Trp Val Pro
 1               5                  10                  15

Gly Ser Thr Gly Asp Ala Ala Gln Pro Ala Arg Arg Ala Val Arg Ser
                20                  25                  30

Leu Cys Pro Gly Ala Cys Val Cys Tyr Asn Glu Pro Lys Val Thr Thr
            35                  40                  45

Ser Cys Pro Gln Gln Gly Leu Gln Ala Val Pro Val Gly Ile Pro Ala
        50                  55                  60

Ala Ser Gln Arg Ile Phe Leu His Gly Asn Arg Ile Ser His Val Pro
 65                  70                  75                  80

Ala Ala Ser Phe Arg Ala Cys Arg Asn Leu Thr Ile Leu Trp Leu His
                85                  90                  95

Ser Asn Val Leu Ala Arg Ile Asp Ala Ala Ala Phe Thr Gly Leu Ala
               100                 105                 110

Leu Leu Glu Gln Leu Asp Leu Ser Asp Asn Ala Gln Leu Arg Ser Val
           115                 120                 125

Asp Pro Ala Thr Phe His Gly Leu Gly Arg Leu His Thr Leu His Leu
       130                 135                 140

Asp Arg Cys Gly Leu Gln Glu Leu Gly Pro Gly Leu Phe Arg Gly Leu
145                 150                 155                 160

Ala Ala Leu Gln Tyr Leu Tyr Leu Gln Asp Asn Ala Leu Gln Ala Leu
               165                 170                 175

Pro Asp Asp Thr Phe Arg Asp Leu Gly Asn Leu Thr His Leu Phe Leu
           180                 185                 190

His Gly Asn Arg Ile Ser Ser Val Pro Glu Arg Ala Phe Arg Gly Leu
       195                 200                 205

His Ser Leu Asp Arg Leu Leu Leu His Gln Asn Arg Val Ala His Val
   210                 215                 220

His Pro His Ala Phe Arg Asp Leu Gly Arg Leu Met Thr Leu Tyr Leu
225                 230                 235                 240

Phe Ala Asn Asn Leu Ser Ala Leu Pro Thr Glu Ala Leu Ala Pro Leu
               245                 250                 255
```

```
Arg Ala Leu Gln Tyr Leu Arg Leu Asn Asp Asn Pro Trp Val Cys Asp
            260                 265                 270

Cys Arg Ala Arg Pro Leu Trp Ala Trp Leu Gln Lys Phe Arg Gly Ser
        275                 280                 285

Ser Ser Glu Val Pro Cys Ser Leu Pro Gln Arg Leu Ala Gly Arg Asp
290                 295                 300

Leu Lys Arg Leu Ala Ala Asn Asp Leu Gln Gly Cys Ala Val Ala Thr
305                 310                 315                 320

Gly Pro Tyr His Pro Ile Trp Thr Gly Arg Ala Thr Asp Glu Glu Pro
                325                 330                 335

Leu Gly Leu Pro Lys Cys Cys Gln Pro Asp Ala Ala Asp Lys Ala Ser
                340                 345                 350

Val Leu Glu Pro Gly Arg Pro Ala Ser Ala Gly Asn Ala Leu Lys Gly
            355                 360                 365

Arg Val Pro Pro Gly Asp Ser Pro Pro Gly Asn Gly Ser Gly Pro Arg
        370                 375                 380

His Ile Asn Asp Ser Pro Phe Gly Thr Leu Pro Gly Ser Ala Glu Pro
385                 390                 395                 400

Pro Leu Thr Ala Val Arg Pro Glu Gly Ser Glu Pro Pro Gly Phe Pro
                405                 410                 415

Thr Ser Gly Pro Arg Arg Pro Gly Cys Ser Arg Lys Asn Arg Thr
                420                 425                 430

Arg Ser His Cys Arg Leu Gly Gln Ala Gly Ser Gly Gly Gly Gly Thr
        435                 440                 445

Gly Asp Ser Glu Gly Ser Gly Ala Leu Pro Arg Ile Leu Gln Ile Ser
450                 455                 460

Ser Thr Val Ala Ala Arg Gly Gly Pro Glu Gln Lys Leu Ile Ser
465                 470                 475                 480

Glu Glu Asp Leu Asn Ser Ala Val Asp His His His His His
                485                 490                 495

<210> SEQ ID NO 2
<211> LENGTH: 498
<212> TYPE: PRT
<213> ORGANISM: Rattus norvegicus

<400> SEQUENCE: 2

Met Lys Arg Ala Ser Ser Gly Gly Ser Arg Leu Leu Ala Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Thr Gly Ile Pro Ala Ser Ser Gln Arg Ile Phe Leu
    50                  55                  60

His Gly Asn Arg Ile Ser Tyr Val Pro Ala Ala Ser Phe Gln Ser Cys
65                  70                  75                  80

Arg Asn Leu Thr Ile Leu Trp Leu His Ser Asn Ala Leu Ala Gly Ile
                85                  90                  95

Asp Ala Ala Ala Phe Thr Gly Leu Thr Leu Leu Glu Gln Leu Asp Leu
            100                 105                 110

Ser Asp Asn Ala Gln Leu Arg Val Val Asp Pro Thr Thr Phe Arg Gly
        115                 120                 125

Leu Gly His Leu His Thr Leu His Leu Asp Arg Cys Gly Leu Gln Glu
    130                 135                 140
```

```
Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
            165                 170                 175

Leu Gly Asn Leu Thr His Leu Phe Leu His Gly Asn Arg Ile Pro Ser
        180                 185                 190

Val Pro Glu His Ala Phe Arg Gly Leu His Ser Leu Asp Arg Leu Leu
    195                 200                 205

Leu His Gln Asn His Val Ala Arg Val His Pro His Ala Phe Arg Asp
210                 215                 220

Leu Gly Arg Leu Met Thr Leu Tyr Leu Phe Ala Asn Asn Leu Ser Met
225                 230                 235                 240

Leu Pro Ala Glu Val Leu Val Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Asn
        275                 280                 285

Leu Pro Gln Arg Leu Ala Gly Arg Asp Leu Lys Arg Leu Ala Ala Ser
290                 295                 300

Asp Leu Glu Gly Cys Ala Val Ala Ser Gly Pro Phe Arg Pro Phe Gln
305                 310                 315                 320

Thr Asn Gln Leu Thr Asp Glu Glu Leu Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
370                 375                 380

Gly Thr Leu Pro Gly Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Ser Ser Gly Thr Gly Asp Ala Glu Gly Ser Gly
        435                 440                 445

Ala Leu Gly Ile Arg Lys Gly Asn Ser Ala Asp Ile Gln His Ser Gly
450                 455                 460

Gly Arg Ser Ser Leu Glu Gly Pro Arg Phe Glu Gly Lys Pro Ile Pro
465                 470                 475                 480

Asn Pro Leu Leu Gly Leu Asp Ser Thr Arg Thr Gly His His His His
                485                 490                 495

His His
```

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      VH antibody clone 50

<400> SEQUENCE: 3

```
Gln Val Gln Leu Gln Gln Pro Gly Ile Glu Val Val Lys Pro Gly Ala
 1               5                  10                  15

Ser Val Lys Leu Ser Cys Lys Ala Ser Gly Tyr Thr Phe Ile Ser Asn
            20                  25                  30

Trp Met His Trp Leu Arg Gln Arg Pro Gly Gln Gly Leu Glu Trp Ile
        35                  40                  45

Gly Glu Ile Asp Pro Ser Asp Thr Tyr Thr Asp Tyr Asn Gln Lys Phe
    50                  55                  60

Lys Gly Lys Ala Thr Leu Thr Val Asp Lys Ser Ser Thr Thr Ala Tyr
65                  70                  75                  80

Met Leu Leu Ser Ser Leu Thr Ser Glu Asp Ser Ala Val Tyr Phe Cys
                85                  90                  95

Ala Arg Gly Gly Met Ile Val Tyr Val Leu Asp Ser Trp Gly Gln Gly
            100                 105                 110

Thr Ser Val Thr Val Ser Ser
            115

<210> SEQ ID NO 4
<211> LENGTH: 114
<212> TYPE: PRT
<213> ORGANISM: Artificial Sequence
<220> FEATURE:
<223> OTHER INFORMATION: Description of Artificial Sequence: Synthetic
      VL antibody clone 50

<400> SEQUENCE: 4

Asp Ile Val Met Tyr Gln Ser Pro Ser Ser Leu Ala Met Ser Val Gly
 1               5                  10                  15

Gln Lys Val Ile Met Asn Cys Lys Ser Ser Gln Ser Leu Leu Ser Ser
            20                  25                  30

Asn Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Asp Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Thr Thr Pro Leu Thr Phe Gly Ala Gly Thr Lys Leu Glu Leu
            100                 105                 110

Lys Arg

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      VH antibody clone 51

<400> SEQUENCE: 5

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Ile Thr Tyr
            20                  25                  30

Trp Met His Trp Met Lys Gln Arg Pro Gly Gln Gly Leu Glu Trp Ile
        35                  40                  45

Gly Glu Ile Asp Pro Ser Asp Ser Tyr Thr Asp Tyr Asn Gln Lys Phe
    50                  55                  60
```

```
Lys Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Ser Asn Val Leu Tyr Val Leu Asp Tyr Trp Gly Gln Gly
            100                 105                 110

Thr Ser Val Thr Val Ser Ser
        115

<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      VL antibody clone 51

<400> SEQUENCE: 6

Asp Ile Val Met Thr Gln Ser Pro Ser Ser Leu Ala Met Ser Val Gly
  1               5                  10                  15

Gln Lys Val Thr Met Ser Cys Lys Ser Ser Gln Ser Leu Leu Asn Ser
                 20                  25                  30

Arg Asn Gln Lys Asn Tyr Leu Ala Trp Tyr Gln Gln Lys Pro Gly Gln
             35                  40                  45

Ser Pro Lys Leu Leu Leu Tyr Phe Ala Ser Thr Arg Glu Ser Gly Val
     50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Thr Thr Pro Leu Thr Phe Gly Ala Gly Thr Lys Glu Leu Lys
            100                 105                 110

Arg

<210> SEQ ID NO 7
<211> LENGTH: 631
<212> TYPE: PRT
<213> ORGANISM: Artificial Sequence
<220> FEATURE:
<223> OTHER INFORMATION: Description of Artificial Sequence: Synthetic
      AP-Nogo66 protein construct

<400> SEQUENCE: 7

Met Glu Thr Asp Thr Leu Leu Leu Trp Val Leu Leu Leu Trp Val Pro
  1               5                  10                  15

Gly Ser Thr Gly Asp Ala Ala Gln Pro Ala Arg Arg Ala Arg Arg Thr
                 20                  25                  30

Tyr Glu Ala Tyr Val Arg Ser Ser Gly Ile Ile Pro Val Glu Glu Glu
             35                  40                  45

Asn Pro Asp Phe Trp Asn Arg Glu Ala Ala Glu Ala Leu Gly Ala Ala
     50                  55                  60

Lys Lys Leu Gln Pro Ala Gln Thr Ala Ala Lys Asn Leu Ile Ile Phe
 65                  70                  75                  80

Leu Gly Asp Gly Met Gly Val Ser Thr Val Thr Ala Ala Arg Ile Leu
                 85                  90                  95

Lys Gly Gln Lys Lys Asp Lys Leu Gly Pro Glu Ile Pro Leu Ala Met
            100                 105                 110

Asp Arg Phe Pro Tyr Val Ala Leu Ser Lys Thr Tyr Asn Val Asp Lys
```

```
            115                 120                 125
His Val Pro Asp Ser Gly Ala Thr Ala Thr Ala Tyr Leu Cys Gly Val
130                 135                 140

Lys Gly Asn Phe Gln Thr Ile Gly Leu Ser Ala Ala Arg Phe Asn
145                 150                 155                 160

Gln Cys Asn Thr Thr Arg Gly Asn Glu Val Ile Ser Val Met Asn Arg
                165                 170                 175

Ala Lys Lys Ala Gly Lys Ser Val Gly Val Thr Thr Arg Val
            180                 185                 190

Gln His Ala Ser Pro Ala Gly Thr Tyr Ala His Thr Val Asn Arg Asn
        195                 200                 205

Trp Tyr Ser Asp Ala Asp Val Pro Ala Ser Ala Arg Gln Glu Gly Cys
    210                 215                 220

Gln Asp Ile Ala Thr Gln Leu Ile Ser Asn Met Asp Ile Asp Val Ile
225                 230                 235                 240

Leu Gly Gly Gly Arg Lys Tyr Met Phe Arg Met Gly Thr Pro Asp Pro
                245                 250                 255

Glu Tyr Pro Asp Asp Tyr Ser Gln Gly Gly Thr Arg Leu Asp Gly Lys
                260                 265                 270

Asn Leu Val Gln Glu Trp Leu Ala Lys Arg Gln Gly Ala Arg Tyr Val
            275                 280                 285

Trp Asn Arg Thr Glu Leu Met Gln Ala Ser Leu Asp Pro Ser Val Thr
    290                 295                 300

His Leu Met Gly Leu Phe Glu Pro Gly Asp Met Lys Tyr Glu Ile His
305                 310                 315                 320

Arg Asp Ser Thr Leu Asp Pro Ser Leu Met Glu Met Thr Glu Ala Ala
                325                 330                 335

Leu Arg Leu Leu Ser Arg Asn Pro Arg Gly Phe Phe Leu Phe Val Glu
            340                 345                 350

Gly Gly Arg Ile Asp His Gly His His Glu Ser Arg Ala Tyr Arg Ala
        355                 360                 365

Leu Thr Glu Thr Ile Met Phe Asp Asp Ala Ile Glu Arg Ala Gly Gln
    370                 375                 380

Leu Thr Ser Glu Glu Asp Thr Leu Ser Leu Val Thr Ala Asp His Ser
385                 390                 395                 400

His Val Phe Ser Phe Gly Gly Tyr Pro Leu Arg Gly Ser Ser Ile Phe
                405                 410                 415

Gly Leu Ala Pro Gly Lys Ala Arg Asp Arg Lys Ala Tyr Thr Val Leu
            420                 425                 430

Leu Tyr Gly Asn Gly Pro Gly Tyr Val Leu Lys Asp Gly Ala Arg Pro
        435                 440                 445

Asp Val Thr Glu Ser Glu Ser Gly Ser Pro Glu Tyr Arg Gln Gln Ser
    450                 455                 460

Ala Val Pro Leu Asp Glu Glu Thr His Ala Gly Glu Asp Val Ala Val
465                 470                 475                 480

Phe Ala Arg Gly Pro Gln Ala His Leu Val His Gly Val Gln Glu Gln
                485                 490                 495

Thr Phe Ile Ala His Val Met Ala Phe Ala Ala Cys Leu Glu Pro Tyr
            500                 505                 510

Thr Ala Cys Asp Leu Ala Pro Pro Ala Gly Thr Thr Asp Ala Ala His
        515                 520                 525

Pro Gly Tyr Leu Glu Glu Ala Leu Ser Leu Glu Arg Ile Tyr Lys Gly
    530                 535                 540
```

```
Val Ile Gln Ala Ile Gln Lys Ser Asp Glu Gly His Pro Phe Arg Ala
545                 550                 555                 560

Tyr Leu Glu Ser Glu Val Ala Ile Ser Glu Glu Leu Val Gln Lys Tyr
                565                 570                 575

Ser Asn Ser Ala Leu Gly His Val Asn Cys Thr Ile Lys Glu Leu Arg
            580                 585                 590

Arg Leu Phe Leu Val Asp Asp Leu Val Asp Ser Leu Lys Ser Leu Glu
        595                 600                 605

Gly Pro Glu Gln Lys Leu Ile Ser Glu Glu Asp Leu Asn Ser Ala Val
    610                 615                 620

Asp His His His His His His
625                 630

<210> SEQ ID NO 8
<211> LENGTH: 1488
<212> TYPE: DNA
<213> ORGANISM: Homo sapiens

<400> SEQUENCE: 8
atggagacag acacactcct gctatgggta ctgctgctct gggttccagg ttccactggt      60
gacgcggccc agccggccag gcgcgccgta cgaagcttat gcccaggtgc ctgcgtatgc     120
tacaatgagc ccaaggtgac gacaagctgc ccccagcagg gcctgcaggc tgtgcccgtg     180
ggcatccctg ctgccagcca gcgcatcttc ctgcacggca accgcatctc gcatgtgcca     240
gctgccagct tccgtgcctg ccgcaacctc accatcctgt ggctgcactc gaatgtgctg     300
gcccgaattg atgcggctgc cttcactggc ctggccctcc tggagcagct ggacctcagc     360
gataatgcac agctccggtc tgtggaccct gccacattcc acggcctggg ccgcctacac     420
acgctgcacc tggaccgctg cggcctgcag gagctgggcc cggggctgtt ccgcggcctg     480
gctgccctgc agtacctcta cctgcaggac aacgcgctgc aggcactgcc tgatgacacc     540
ttccgcgacc tgggcaacct cacacacctc ttcctgcacg gcaaccgcat ctccagcgtg     600
cccgagcgcg ccttccgtgg gctgcacagc ctcgaccgtc tcctactgca ccagaaccgc     660
gtggcccatg tgcacccgca tgccttccgt gaccttggcc gcctcatgac actctatctg     720
tttgccaaca atctatcagc gctgcccact gaggccctgg cccccctgcg tgccctgcag     780
tacctgaggc tcaacgacaa ccccctgggtg tgtgactgcc gggcacgccc actctgggcc     840
tggctgcaga gttccgcgg ctcctcctcc gaggtgccct gcagcctccc gcaacgcctg     900
gctggccgtg acctcaaacg cctagctgcc aatgacctgc agggctgcgc tgtggccacc     960
ggcccttacc atcccatctg accggcagg gccaccgatg aggagccgct ggggcttccc    1020
aagtgctgcc agccagatgc cgctgacaag gcctcagtac tggagcctgg aagaccagct    1080
tcggcaggca atgcgctgaa gggacgcgtg ccgcccggtg acagcccgcc gggcaacggc    1140
tctgccccac ggcacatcaa tgactcaccc tttgggactc tgcctggctc tgctgagccc    1200
ccgctcactg cagtgcggcc cgagggctcc gagccaccag ggttccccac ctcgggccct    1260
cgccggaggc caggctgttc acgcaagaac cgcaccccgca gccactgccg tctgggccag    1320
gcaggcagcg ggggtggcgg gactggtgac tcagaaggct caggtgccct acccagaatt    1380
ctgcagatat ccagcacagt ggcggccgct cgaggagggc cgaacaaaaa actcatctca    1440
gaagaggatc tgaatagcgc cgtcgaccat catcatcatc atcattga                 1488

<210> SEQ ID NO 9
<211> LENGTH: 1497
<212> TYPE: DNA
```

-continued

<213> ORGANISM: Rattus norvegicus

<400> SEQUENCE: 9

```
atgaagaggg cgtcctccgg aggaagccgg ctgctggcat gggtgttatg gctacaggcc      60
tggagggtag caacgccctg ccctggtgcc tgtgtgtgct acaatgagcc caaggtcaca     120
acaagctgcc cccagcaggg cctgcaggct gtacccactg gcatcccagc ctccagccag     180
agaatcttcc tgcacggcaa ccgaatctct tacgtgccag ccgccagctt ccagtcatgc     240
cggaatctca ccatcctgtg gctgcactca aatgcgctgg ccgggattga tgccgcggcc     300
ttcactggtc tgaccctcct ggagcaacta gatcttagtg acaatgcaca gctccgtgtc     360
gtggacccca ccacgttccg tggcctgggc cacctgcaca cgctgcacct agaccgatgc     420
ggcctgcagg agctggggcc tggcctattc cgtgggctgg cagctctgca gtacctctac     480
ctacaagaca caacctgca ggcacttccc gacaacacct tccgagacct gggcaacctc      540
acgcatctct ttctgcatgg caaccgtatc cccagtgttc ctgagcacgc tttccgtggc     600
ttgcacagtc ttgaccgtct cctcttgcac agaaccatg tggctcgtgt gcacccacat      660
gccttccggg accttggccg actcatgacc ctctacctgt tgccaacaa cctctccatg      720
ctccccgcag aggtcctagt gcccctgagg tctctgcagt acctgcgact caatgacaac     780
ccctgggtgt gtgactgcag ggcacgtccg ctctgggcct ggctgcagaa gttccgaggt     840
tcctcatccg aggtgccctg caacctaccc caacgcctgg caggccgtga tctgaagcgc     900
ctggctgcca gtgacttaga ggggttgtgct gtggcttcgg ggcccttccg tcccttccag     960
accaatcagc tcactgatga ggagctgctg ggcctcccca gtgctgccca gccggatgct    1020
gcagacaagg cctcagtact ggaacccggg aggccggcgt ctgctggaaa tgcactcaag    1080
ggacgtgtgc ctcccggtga cactccacca ggcaatggct caggcccacg gcacatcaat    1140
gactctccat ttgggacttt gccgggctct gcagagcccc cactgactgc cctgcgcct    1200
ggggggttccg agccccgggg actgcccacc acgggtcccc gcaggaggcc aggttgttcc   1260
agaaagaacc gcacccgtag ccactgccgt ctgggccagg caggaagtgg gagcagtgga   1320
actggggatg cagaaggttc ggggggccctg ggaattcgga agggcaattc tgcagatatc   1380
cagcacagtg gcggccgctc gagtctagag ggcccgcggt tcgaaggtaa gcctatccct   1440
aacctcctcc tcggtctcga ttctacgcgt accggtcatc atcaccatca ccattga      1497
```

<210> SEQ ID NO 10
<211> LENGTH: 1896
<212> TYPE: DNA
<213> ORGANISM: Artificial Sequence
<220> FEATURE:
<223> OTHER INFORMATION: Description of Artificial Sequence: Synthetic
      AP-Nogo66 nucleotide construct

<400> SEQUENCE: 10

```
atggagacag acacactcct gctatgggta ctgctgctct gggttccagg ttccactggt      60
gacgcggccc agccggccag gcgcgcgcgc cgtacgtacg aagcttacgt aagatcttcc     120
ggaatcatcc cagttgagga ggagaacccg gacttctgga accgcgaggc agccgaggcc     180
ctgggtgccg ccaagaagct gcagcctgca cagacagccg ccaagaacct catcatcttc     240
ctgggcgatg ggatggggt gtctacggtg acagctgcca ggatcctaaa agggcagaag     300
aaggacaaac tgggcctga gatacccctg ccatggacc gcttcccata tgtggctctg     360
tccaagacat acaatgtaga caaacatgtg ccagacagtg agccacagc cacggcctac     420
ctgtgcgggg tcaagggcaa cttccagacc attggcttga gtgcagccgc ccgctttaac     480
```

```
cagtgcaaca cgacacgcgg caacgaggtc atctccgtga tgaatcgggc caagaaagca    540
gggaagtcag tgggagtggt aaccaccaca cgagtgcagc acgcctcgcc agccggcacc    600
tacgcccaca cggtgaaccg caactggtac tcggacgccg acgtgcctgc ctcggcccgc    660
caggaggggt gccaggacat cgctacgcag ctcatctcca acatggacat tgacgtgatc    720
ctaggtggag gccgaaagta catgtttcgc atgggaaccc cagaccctga gtacccagat    780
gactacagcc aaggtgggac caggctggac gggaagaatc tggtgcagga atggctggcg    840
aagcgccagg gtgcccggta tgtgtggaac cgcactgagc tcatgcaggc ttccctggac    900
ccgtctgtga cccatctcat gggtctcttt gagcctggag acatgaaata cgagatccac    960
cgagactcca cactggaccc ctccctgatg gagatgacag aggctgccct gcgcctgctg   1020
agcaggaacc cccgcggctt cttcctcttc gtggagggtg gtcgcatcga ccatggtcat   1080
catgaaagca gggcttaccg ggcactgact gagacgatca tgttcgacga cgccattgag   1140
agggcgggcc agctcaccag cgaggaggac acgctgagcc tcgtcactgc cgaccactcc   1200
cacgtcttct ccttcggagg ctaccccctg cgagggagct ccatcttcgg gctggcccct   1260
ggcaaggccc gggacaggaa ggcctacacg gtcctcctat acgaaacggt ccaggctat   1320 gtgctcaagg acggcgcccg gccggatgtt accgagagcg agagcgggag ccccgagtat   1380
cggcagcagt cagcagtgcc cctggacgaa gagacccacg caggcgagga cgtggcggtg   1440
ttcgcgcgcg gcccgcaggc gcacctggtt cacggcgtgc aggagcagac cttcatagcg   1500
cacgtcatgg ccttcgccgc ctgcctggag ccctacaccg cctgcgacct ggcgccccc   1560 gccggcacca ccgacgccgc gcacccgggt tatctcgagg aagcgctctc tctagaaagg   1620
atatacaagg gtgtgatcca agctatccag aaatcagatg aaggccaccc attcagggca   1680
tatctggaat ctgaagttgc tatatctgag gagttggttc agaagtacag taattctgct   1740
cttggtcatg tgaactgcac gataaaggaa ctcaggcgcc tcttcttagt tgatgattta   1800
gttgattctc tgaagtctct agaagggccc gaacaaaaac tcatctcaga gaggatctg   1860 aatagcgccg tcgaccatca tcatcatcat cattga                            1896
```

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 11

Gly Gly Gly Gly Ser
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 12

His His His His His His
 1               5

<210> SEQ ID NO 13
<211> LENGTH: 54

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gccaggcgcg ccgtacgaag cttatgcgcc agccagcgca tcttcctgca cggc          54

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccgtgcagg aagatgcgct ggctggcgca taagcttcgt acggcgcgcc tggc          54

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gctgtgcccg tgggcatccc tgctgccctc ctggagcagc tggacctcag cgataatgc     59

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcattatcgc tgaggtccag ctgctccagg agggcagcag ggatgcccac gggcacagc     59

<210> SEQ ID NO 17
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcggctgcct tcactggcct ggccgccctg cagtacctct acctgcagga caacgc        56

<210> SEQ ID NO 18
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcgttgtcct gcaggtagag gtactgcagg gcggccaggc cagtgaaggc agccgc        56

<210> SEQ ID NO 19
<211> LENGTH: 56
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 19
cggggctgtt ccgcggcctg gctagcctcg accgtctcct actgcaccag aaccgc         56

<210> SEQ ID NO 20
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcggttctgg tgcagtagga gacggtcgag gctagccagg ccgcggaaca gccccg         56

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gagcgcgcct tccgtgggct gcacgccctg cagtacctga ggctcaacga caacc          55

<210> SEQ ID NO 22
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggttgtcgtt gagcctcagg tactgcaggg cgtgcagccc acggaaggcg cgctc          55

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcgtgccctg cagtacctga ggctcaacga cgtggccacc ggcccttacc atcccatctg     60

<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagatgggat ggtaagggcc ggtggccacg tcgttgagcc tcaggtactg ca             52

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
```

-continued

```
      primer

<400> SEQUENCE: 25
ccccaagctt atgcccaggt gcctgc                                              26

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccccgaattc cagcgcagcc ctgcaggtc                                           29
```